US009198874B2

(12) United States Patent
Zale et al.

(10) Patent No.: US 9,198,874 B2
(45) Date of Patent: *Dec. 1, 2015

(54) LONG CIRCULATING NANOPARTICLES FOR SUSTAINED RELEASE OF THERAPEUTIC AGENTS

(71) Applicant: BIND Therapeutics, Inc., Cambridge, MA (US)

(72) Inventors: Stephen E. Zale, Hopkinton, MA (US); Greg Troiano, Pembroke, MA (US); Mir Mukkaram Ali, Woburn, MA (US); Jeff Hrkach, Lexington, MA (US); James Wright, Lexington, MA (US)

(73) Assignee: BIND Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/100,695

(22) Filed: Dec. 9, 2013

(65) Prior Publication Data

US 2014/0093579 A1 Apr. 3, 2014

Related U.S. Application Data

(63) Continuation of application No. 13/556,647, filed on Jul. 24, 2012, which is a continuation of application No. 12/638,297, filed on Dec. 15, 2009, now abandoned.

(60) Provisional application No. 61/122,479, filed on Dec. 15, 2008, provisional application No. 61/249,022, filed on Oct. 6, 2009, provisional application No. 61/260,200, filed on Nov. 11, 2009.

(51) Int. Cl.
| | |
|---|---|
| A61K 9/51 | (2006.01) |
| A61K 47/34 | (2006.01) |
| B82Y 5/00 | (2011.01) |
| A61K 9/00 | (2006.01) |
| A61K 47/48 | (2006.01) |

(52) U.S. Cl.
CPC ............ *A61K 9/5153* (2013.01); *A61K 9/0019* (2013.01); *A61K 47/48869* (2013.01); *A61K 47/48915* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 5,302,401 A | 4/1994 | Liversidge et al. |
| 5,543,158 A | 8/1996 | Gref et al. |
| 5,563,122 A | 10/1996 | Endo et al. |
| 5,578,325 A | 11/1996 | Domb et al. |
| 5,766,635 A | 6/1998 | Spenleuhauer et al. |
| 6,007,845 A | 12/1999 | Domb et al. |
| 6,136,846 A | 10/2000 | Rubinfeld et al. |
| 6,139,870 A | 10/2000 | Verrecchia |
| 6,201,072 B1 | 3/2001 | Rathi et al. |
| 6,254,890 B1 | 7/2001 | Hirosue et al. |
| 6,265,609 B1 | 7/2001 | Jackson et al. |
| 6,346,274 B1 | 2/2002 | Koll et al. |
| 6,395,718 B1 | 5/2002 | Slusher et al. |
| 6,528,499 B1 | 3/2003 | Kozikowski et al. |
| 6,841,547 B2 | 1/2005 | Brown et al. |
| 6,875,886 B2 | 4/2005 | Frangioni |
| 6,890,946 B2 | 5/2005 | Nakshatri et al. |
| 6,890,950 B2 | 5/2005 | Boothman et al. |
| 6,902,743 B1 | 6/2005 | Setterstrom et al. |
| 6,916,788 B2 | 7/2005 | Seo et al. |
| 7,422,902 B1 | 9/2008 | Wheeler et al. |
| 8,003,128 B2 | 8/2011 | Kreuter et al. |
| 8,034,765 B2 | 10/2011 | De et al. |
| 8,206,747 B2 | 6/2012 | Zale et al. |
| 8,211,473 B2 | 7/2012 | Troiano et al. |
| 8,236,330 B2 | 8/2012 | Zale et al. |
| 8,246,968 B2 | 8/2012 | Zale et al. |
| 8,273,363 B2 | 9/2012 | Zale et al. |
| 8,293,276 B2 | 10/2012 | Troiano et al. |
| 8,318,208 B1 | 11/2012 | Zale et al. |
| 8,318,211 B2 | 11/2012 | Zale et al. |
| 8,357,401 B2 | 1/2013 | Troiano et al. |
| 8,420,123 B2 | 4/2013 | Troiano et al. |
| 8,518,963 B2 | 8/2013 | Ali et al. |
| 8,623,417 B1 | 1/2014 | Zale et al. |
| 2002/0045582 A1 | 4/2002 | Margolin et al. |
| 2002/0119916 A1 | 8/2002 | Hassan |
| 2003/0068377 A1 | 4/2003 | Fowers et al. |
| 2003/0143184 A1 | 7/2003 | Seo et al. |
| 2003/0232887 A1 | 12/2003 | Johnson et al. |
| 2003/0235619 A1 | 12/2003 | Allen et al. |
| 2004/0054190 A1 | 3/2004 | Pomper et al. |
| 2004/0071768 A1 | 4/2004 | Sarris et al. |
| 2004/0081688 A1 | 4/2004 | Del Curto et al. |
| 2004/0086544 A1 | 5/2004 | Bezemer et al. |

(Continued)

FOREIGN PATENT DOCUMENTS

| | | |
|---|---|---|
| CN | 1957911 A | 5/2007 |
| CN | 1961864 A | 5/2007 |

(Continued)

OTHER PUBLICATIONS

Balabai et al., "Solute—Solvent Frictional Coupling in Electrolyte Solutions. Role of Ion Pairs." *J. Phys. Chem.* (1997) 101:2339-2347.

(Continued)

*Primary Examiner* — Theodore R West
(74) *Attorney, Agent, or Firm* — Goodwin Procter LLP

(57) ABSTRACT

The present disclosure is directed in part to a biocompatible nanoparticle composition comprising a plurality of non-colloidal long circulating nanoparticles, each comprising a α-hydroxy polyester-co-polyether and a therapeutic agent, wherein such disclosed compositions provide a therapeutic effect for at least 12 hours.

11 Claims, 10 Drawing Sheets

(56) References Cited

U.S. PATENT DOCUMENTS

| | | |
|---|---|---|
| 2004/0185170 A1 | 9/2004 | Chungi et al. |
| 2004/0219224 A1 | 11/2004 | Yakovlevsky et al. |
| 2004/0220081 A1 | 11/2004 | Kreitz et al. |
| 2004/0247624 A1 | 12/2004 | Unger et al. |
| 2004/0247680 A1 | 12/2004 | Farokhzad et al. |
| 2005/0037075 A1 | 2/2005 | Farokhzad et al. |
| 2005/0037086 A1 | 2/2005 | Tyo et al. |
| 2005/0063976 A1 | 3/2005 | Schultes et al. |
| 2005/0123617 A1 | 6/2005 | Chang et al. |
| 2005/0136258 A1 | 6/2005 | Nie et al. |
| 2005/0142205 A1 | 6/2005 | Rashba-Step et al. |
| 2005/0201972 A1 | 9/2005 | Seo et al. |
| 2005/0256071 A1 | 11/2005 | Davis |
| 2005/0266067 A1 | 12/2005 | Sengupta et al. |
| 2006/0002852 A1 | 1/2006 | Saltzman et al. |
| 2006/0002971 A1 | 1/2006 | Saltzman et al. |
| 2006/0034925 A1 | 2/2006 | Au et al. |
| 2006/0057219 A1 | 3/2006 | Nagasaki et al. |
| 2006/0110460 A1 | 5/2006 | Ferret et al. |
| 2006/0165987 A1 | 7/2006 | Hildgen et al. |
| 2007/0031402 A1 | 2/2007 | Zhang et al. |
| 2007/0041901 A1 | 2/2007 | Diener et al. |
| 2007/0043066 A1 | 2/2007 | Sum et al. |
| 2007/0053845 A1 | 3/2007 | Sengupta et al. |
| 2007/0154554 A1 | 7/2007 | Burgermeister et al. |
| 2008/0057102 A1 | 3/2008 | Roorda |
| 2008/0081074 A1 | 4/2008 | Gu et al. |
| 2008/0124400 A1 | 5/2008 | Liggins et al. |
| 2008/0193381 A1 | 8/2008 | Babich et al. |
| 2008/0267876 A1 | 10/2008 | Benita et al. |
| 2009/0022806 A1 | 1/2009 | Mousa et al. |
| 2009/0053293 A1 | 2/2009 | Liang et al. |
| 2009/0053315 A1 | 2/2009 | Brough et al. |
| 2009/0061009 A1 | 3/2009 | Schwarz et al. |
| 2009/0074753 A1 | 3/2009 | Lynch |
| 2009/0074828 A1 | 3/2009 | Alexis et al. |
| 2009/0155349 A1 | 6/2009 | Heller et al. |
| 2009/0170753 A1 | 7/2009 | Welz et al. |
| 2009/0306120 A1 | 12/2009 | Lim et al. |
| 2009/0317479 A1 | 12/2009 | Ishihara et al. |
| 2010/0008998 A1 | 1/2010 | Kang et al. |
| 2010/0015050 A1 | 1/2010 | Panyam et al. |
| 2010/0040537 A1 | 2/2010 | Gu et al. |
| 2010/0068286 A1 | 3/2010 | Troiano et al. |
| 2010/0069426 A1 | 3/2010 | Zale et al. |
| 2010/0087337 A1 | 4/2010 | Dewitt |
| 2010/0104645 A1 | 4/2010 | Ali et al. |
| 2010/0104655 A1 | 4/2010 | Zale et al. |
| 2010/0166866 A1 | 7/2010 | Fischer et al. |
| 2010/0216804 A1 | 8/2010 | Zale et al. |
| 2010/0226986 A1 | 9/2010 | Grayson et al. |
| 2010/0266491 A1 | 10/2010 | Farokhzad et al. |
| 2010/0303723 A1 | 12/2010 | Farokhzad et al. |
| 2010/0303900 A1 | 12/2010 | Ramstack et al. |
| 2010/0316725 A1 | 12/2010 | Ryde et al. |
| 2011/0159079 A1 | 6/2011 | Li et al. |
| 2011/0217377 A1 | 9/2011 | Zale et al. |
| 2011/0275704 A1 | 11/2011 | Troiano et al. |
| 2011/0294717 A1 | 12/2011 | Ali et al. |
| 2012/0140790 A1 | 6/2012 | Ali et al. |
| 2012/0276162 A1 | 11/2012 | Zale et al. |
| 2013/0034608 A1 | 2/2013 | Zale et al. |
| 2013/0101672 A1 | 4/2013 | Cheng et al. |
| 2013/0108668 A1 | 5/2013 | Figueiredo et al. |
| 2013/0115293 A1 | 5/2013 | Sabnis et al. |
| 2013/0172406 A1 | 7/2013 | Zale et al. |
| 2013/0189315 A1 | 7/2013 | Zale et al. |
| 2013/0230567 A1 | 9/2013 | Zale et al. |
| 2013/0230568 A1 | 9/2013 | Troiano et al. |
| 2013/0236500 A1 | 9/2013 | Zale et al. |
| 2013/0243827 A1 | 9/2013 | Troiano et al. |
| 2013/0243863 A1 | 9/2013 | Troiano et al. |
| 2013/0251757 A1 | 9/2013 | Troiano et al. |
| 2013/0280339 A1 | 10/2013 | Zale et al. |
| 2013/0295183 A1 | 11/2013 | Troiano et al. |
| 2013/0295191 A1 | 11/2013 | Troiano et al. |
| 2013/0302432 A1 | 11/2013 | Zale et al. |
| 2013/0302433 A1 | 11/2013 | Troiano et al. |
| 2014/0030351 A1 | 1/2014 | Zale et al. |
| 2014/0093579 A1 | 4/2014 | Zale et al. |
| 2014/0142165 A1 | 5/2014 | Grayson et al. |

FOREIGN PATENT DOCUMENTS

| | | |
|---|---|---|
| CN | 1969816 A | 5/2007 |
| CN | 1969818 A | 5/2007 |
| CN | 101053553 A | 10/2007 |
| CN | 101396340 A | 4/2009 |
| CN | 101396342 A | 4/2009 |
| CN | 101433520 A | 5/2009 |
| EA | 011594 | 12/2007 |
| EP | 0805678 A1 | 11/1997 |
| EP | 1985309 A1 | 10/2008 |
| EP | 2106806 A1 | 10/2009 |
| JP | 2006131577 A | 5/2006 |
| JP | 2006321763 A | 11/2006 |
| KR | 10-0418916 B1 | 3/2002 |
| KR | 20020041712 A | 6/2002 |
| RU | 2007/140909 A | 5/2009 |
| WO | WO-94/28874 A1 | 12/1994 |
| WO | WO-95/03357 A1 | 2/1995 |
| WO | WO-95/35097 A1 | 12/1995 |
| WO | WO-97/41837 A2 | 11/1997 |
| WO | WO-00/00222 A1 | 1/2000 |
| WO | WO-00/19996 A1 | 4/2000 |
| WO | WO-02/080846 A2 | 10/2002 |
| WO | WO-02/098885 A1 | 12/2002 |
| WO | WO-03/017987 A1 | 3/2003 |
| WO | WO-03/032906 A2 | 4/2003 |
| WO | WO-03/055469 A1 | 7/2003 |
| WO | WO-03/086369 A2 | 10/2003 |
| WO | WO-2004/084871 A1 | 10/2004 |
| WO | WO-2004/089291 A2 | 10/2004 |
| WO | WO-2005009357 A2 | 2/2005 |
| WO | WO-2005/020989 A1 | 3/2005 |
| WO | WO-2005/046572 A2 | 5/2005 |
| WO | WO-2006/093991 A1 | 9/2006 |
| WO | WO-2007/024323 A2 | 3/2007 |
| WO | WO-2007/028341 A1 | 3/2007 |
| WO | WO-2007/034479 A2 | 3/2007 |
| WO | WO-2007/074604 A1 | 7/2007 |
| WO | WO-2007/110152 A2 | 10/2007 |
| WO | WO-2007/133807 A2 | 11/2007 |
| WO | WO-2008/019142 A2 | 2/2008 |
| WO | WO-2008/058192 A2 | 5/2008 |
| WO | WO-2008/105773 A2 | 9/2008 |
| WO | WO-2008/121949 A1 | 10/2008 |
| WO | WO-2008/124632 A1 | 10/2008 |
| WO | WO-2008/124634 A1 | 10/2008 |
| WO | WO-2008/124639 A2 | 10/2008 |
| WO | WO-2008/139804 A1 | 11/2008 |
| WO | WO-2009/070302 A1 | 6/2009 |
| WO | WO-2009/074274 A1 | 6/2009 |
| WO | WO-2009/084801 A1 | 7/2009 |
| WO | WO-2009121631 A2 | 10/2009 |
| WO | WO-2010/005721 A2 | 1/2010 |
| WO | WO-2010/005723 A2 | 1/2010 |
| WO | WO-2010/005725 A2 | 1/2010 |
| WO | WO-2010/005726 A2 | 1/2010 |
| WO | WO-2010/068866 A2 | 6/2010 |
| WO | WO-2010/075072 A2 | 7/2010 |
| WO | WO-2010/114768 A1 | 10/2010 |
| WO | WO-2010/114770 A1 | 10/2010 |
| WO | WO-2010/117668 A1 | 10/2010 |
| WO | WO-2011/072218 A2 | 6/2011 |
| WO | WO-2011/079279 A2 | 6/2011 |
| WO | WO-2011/084513 A2 | 7/2011 |
| WO | WO-2011/084518 A2 | 7/2011 |
| WO | WO-2011/084521 A2 | 7/2011 |
| WO | WO-2011/119995 A2 | 9/2011 |
| WO | WO-2012040513 A1 | 3/2012 |
| WO | WO-2012/054923 A2 | 4/2012 |
| WO | WO-2012/166923 A2 | 12/2012 |
| WO | WO-2013/044219 A1 | 3/2013 |

(56) References Cited

FOREIGN PATENT DOCUMENTS

| WO | WO-2013127490 A1 | 9/2013 |
|---|---|---|
| WO | WO-2014043618 A1 | 3/2014 |
| WO | WO-2014043625 A1 | 3/2014 |

OTHER PUBLICATIONS

Definition of "coupled" from the Oxford English Dictionary (retrieved from oed.com on Jun. 13, 2013) 2 pages.
International Search Report for Application No. PCT/US2013/059949, dated Jan. 2, 2014 and mailed Jan. 2, 2014, 5 pages.
Kimura et al., "Local Delivery of Imatinib Mesylate (STI571)-Incorporated Nanoparticle Ex Vivo Suppresses Vein Graft Neointima Formation," *Cancer Res.* (2008) 118:S65-S70.
Li et al., "Post-Operative Imatinib in Patients with Intermediate or High Risk Gastrointestinal Stromal Tumor," *EJSO.* (2011) 37:319-324.
Abdelwahed et al., "Freeze-Drying of Nanoparticles: Formulation, Process and Storage Considerations," *Adv. Drug Deliv. Rev.* (2006) 58:1688-1713.
Abizaid et al., "Sirolimus-Eluting Stents Inhibits Neointimal Hyperplasia in Diabetic Patients," *Eur. Heart J.* (2006) 25:104-112.
Adams et al., "Amphiphilic Block Copolymers for Drug Delivery", *J. Pharm. Sci.* (2003) 92, 1343-1355.
Avgoustakis, "Pegylated poly(lactide) and poly(lactide-co-glycolide) nanoparticles: Preparation, properties and possible applications in drug delivery," *Current Drug Delivery.* (2004) 1(4):321-333.
Barinka et al., "Interactions Between Human Glutamate Carboxypeptidase II and Urea-Based Inhibitors: Structural Characterization," *J. Med. Chem.* (2008) 51:7737-7743.
Barinka et al., "Structural Insight into the Pharmacophore Pocket of Human Glutamate Carboxypeptidase II, " *J. Med. Chem.* (2007) 50:3267-3273.
Bilati et al., "Nanoprecipitation Versus Emulsion-based Techniques for the Encapsulation of Proteins into Biodegradable Nanoparticles and Process-related Stability Issues," AAPS *PharmSciTech.* (2005) 6(4):E594-E604.
Blindt et al., "A Novel Drug-Eluting Stent Coated with an Integrin-Binding Cyclic Arg-Gly-Asp Peptide Inhibits Neointimal Hyperplasia by Recruiting Endothelial Progenitor Cells " *J. Amer. Coll. Cardiol.* (2006) 47(9):1786-1795.
Caliceti et al., "Effective Protein Release from PEG/PLA Nanoparticles Produced by Compressed Gas Anti-Solvent Precipitation Techniques," *Journal of Controlled Release.* (2004) 94:195-205.
Chandran, et al., "Characterization of a Targeted Nanoparticle Functionalized with a Urea-Based Inhibitor of Prostate-Specific Membrane Antigen (PSMA)," *Cancer Biol. Ther.* (2008) 7:4:1-9.
Chen et al., "Radiohalogenated Prostate-Specific Membrane Antigen (PSMA)-Based Ureas as Imaging Agents for Prostate Cancer," *J. Med. Chem.* (2008) 51(24):7933-7943.
Cheng et al., "Formulation of Functionalized PLGA-PEG Nanoparticles for in Vivo Targeted Drug Delivery," *Biomaterials.* (2007) 28:869-879.
Dancey et al., "Therapeutic Targets mTOR and Related Pathways," *Cancer Biol. Ther.* (2006) 5:9: 1065-1073.
Davaran, "Preparation and in Vitro Evaluation of Linear and Star-Branched PLGA Nanoparticles for Insulin Delivery," *J. Bioact. Compat. Polym.* (2008) 23:115-131.
De Jaeghere et al., "Formulation and Lyoprotection of Poly(lactic acid-co-ethylene oxide) Nanoparticles: Influence on Physical Stability and in Vitro Cell Uptake," *Pharm. Res.* (1999) 16(6):859-866.
De Jaeghere et al., "Freeze-Drying and Lyopreservation of Diblock and Triblock Poly(Lactic Acid)-Poly(Ethylene Oxide) (PLA-PEO) Copolymer Nanoparticles," *Pharmaceutical Development and Technology.* (2000) 5(4):473-483.
"Docetaxel Dosage," [retrieved on Mar. 28, 2013] http://www.drugs.com/dosage/docetaxel.html.

Dong et al., "In vitro and in vivo evaluation of methoxy polyethylene glycol-polylactide (MPEG-PLA) nanoparticles for small-molecule drug chemotherapy," (2007) Biomaterials.
Eurasian Search Report for Application No. EA 201170038, dated Jul. 8, 2011.
Eurasian Search Report for Application No. EA 201170039, dated Nov. 21, 2011.
Eurasian Search Report for Application No. EA 201100765, dated Aug. 2, 2013.
Eurasian Official Action for EA 201170038, dated Aug. 12, 2013.
Ewesuedo et al., "Chapter 1: Systemically Administrated Drugs." *Drug Delivery Systems in Cancer Therapy.* Ed. D.M. Brown Totowa:Humana, 2003, pp. 3-14.
Extended European Search Report for Application No. EP 09794913.5 mailed Jul. 8, 2011.
Extended European Search Report for Application No. EP 09794915.0, mailed Jan. 25, 2012.
Extended European Search Report for Application No. EP 09835578.7, mailed May 18, 2012.
Extended European Search Report for Application No. EP 10836748.3, mailed Mar. 21, 2013.
Farokhzad et al., "Nanoparticle-Aptamer Bioconjugates: A New Approach for Targeting Prostate Cancer Cells," *Cancer Res.* (Nov. 1, 2004) 64:7668-7672.
Farokhzad et al., "Targeted Nanoparticle-Aptamer Bioconjugates for Cancer Chemotherapy in Vivo," *Proc. Natl. Acad. Sci. USA.* (2006) 103(16):6315-6320.
Feng et al., "Nanoparticles of Biodegradable Polymers for Clinical Administration of Paclitaxel," *Current Medicinal Chemistry.* (2004) 11:413-424.
Foss et al., "Radiolabeled Small-Molecule Ligands for Prostate-Specific Membrane Antigen: In Vivo Imaging in Experimental Models of Prostate Cancer," *Clin. Cancer Res.* (2005) 11(11):4022-4028.
Foss, Poster Session: Novel Probes and Activation Strategies, Part 3, "Synthesis and Validation of a Novel Small-Molecule Fluorescent Probe for PSMA Expression in Human Tumor Neovasculature," 4th Annual Meeting for the Society for Molecular Imaging, (Sep. 7-10, 2005.).
Fournier et al., "Experimental Studies and Preliminary Clinical Trial of Vinorelbine-loaded Polymeric Bioresorbable Implants for the Local Treatment of Solid Tumors," *Cancer Research.* (1991) 51:5384-5391.
Galsky et al., "Cabazitaxel," *Nature Reviews.* (2010) 9:677-678.
Gao et al., "In Vivo Cancer Targeting and Imaging with Semiconductor Quantum Dots," *Nat. Biotechnol.* (2004) 22, 8: 969-976.
Gref et al., "'Stealth' Corona-Core Nanoparticles Surface Modified by Polyethylene Glycol (PEG): Influences of the Corona (PEG Chaing Length and Surface Density) and of the Core Composition on Phagocytic Uptake and Plasma Protein Adsorption," *Colloids and Surfaces B: Biointerfaces.* (2000) 301-313.
Govender et al., "Defining the Drug Incorporation Properties of PLA-PEG Nanoparticles," *Int. J. Pharm.* (2000) 199:95-110.
Gref et al., "Biodegradable Long-Circulating Polymeric Nanospheres," *Science.* (1994) 263:1600-1603.
Gref et al., "Development and Characterization of CyA-loaded Poly(lactic acid)-poly(ethylene glycol)PEG Micro- and Nanoparticles. Comparison with Conventional PLA Particulate Carriers." *Eur. J. Pharm. Biopharm.* (2001) 51:111-118.
Gu et al., "Precise Engineering of Targeted Nanoparticles by Using Self-Assembled Biointegrated Block Copolymers", *Proc. Natl. Acad. Sci. USA.* (2008) 105:2586-2591.
Heald et al., "Poly(lactic acid)-Poly(ethylene oxide) (PLA-PEG) Nanoparticles: NMR Studies of the Central Solidlike PLA Core and the Liquid PEG Corona," *Langmuir.* L2002) 18:3669-3675.
Hederstrom et al., "Purification and Surface Modification of Polymeric Nanoparticles for Medical Applications" Master's Thesis. SINTEF Materials and Chemistry, Trondheim, Norway, Mar. 3, 2008.
Heldman et al., "Paclitaxel stent coating inhibits neointimal hyperplasia at 4 weeks in a porcine model of coronary restenosis," *Circulation.* (2001) 103:2289-2295.

(56) References Cited

OTHER PUBLICATIONS

Hrkach et al., "Preclinical Development and Clinical Translation of a PSMA-Targeted Docetaxel Nanoparticle with a Differentiated Pharmacological Profile," *Sci. Trans. Med.* (2012) 4:1-11.

Humblet et al., "An HPLC/Mass Spectrometry Platform for the Development of Multimodality Contrast Agents and Targeted Therapeutics: Prostate-Specific Membrane Antigen Small Molecule Derivatives," *Contrast Med. Mol. Imaging.* (2006) 1:196-211.

Humblet et al., "High-Affinity Near-Infrared Fluorescent Small-Molecule Contrast Agents for in Vivo Imaging of Prostate-Specific Membrane Antigen," *Mol. Imaging.* (2005) 4:448-462.

International Search Report for Application No. PCT/US08/13158 dated Jan. 20, 2009 and mailed Feb. 17, 2009.

International Search Report for Application No. PCT/US08/58873 dated Aug. 15, 2008 and mailed Aug. 28, 2008.

International Search Report for Application No. PCT/US09/47513 dated Jan. 18, 2010 and mailed Jan. 18, 2010.

International Search Report for Application No. PCT/US09/67672 dated Aug. 20, 2010 and mailed Aug. 23, 2010.

International Search Report for Application No. PCT/US09/68028 dated Aug. 9, 2010 and mailed Aug. 23, 2010.

International Search Report for Application No. PCT/US10/59879 dated Aug. 30, 2011 and mailed Aug. 30, 2011.

International Search Report for Application No. PCT/US10/60564 dated Sep. 29, 2011 and mailed Sep. 29, 2011.

International Search Report for Application No. PCT/US10/60570 dated Aug. 25, 2011 and mailed Aug. 25, 2011.

International Search Report for Application No. PCT/US10/60575 dated Aug. 25, 2011 and mailed Aug. 25, 2011.

International Search Report for Application No. PCT/US11/057498 dated May 9, 2012 and mailed May 10, 2012.

International Search Report for Application No. PCT/US2012/040215 dated Nov. 16, 2012 and mailed Nov. 16, 2012.

International Search Report for Application No. PCT/US2012/056891 dated Jan. 4, 2013 and mailed Jan. 4, 2013.

International Search Report for PCT/US09/47515 dated Jan. 18, 2010 and mailed Jan. 19, 2010.

International Search Report for PCT/US09/47517 dated Feb. 23, 2010 and mailed Mar. 2, 2010.

International Search Report for PCT/US09/47518 dated Mar. 5, 2010 and mailed Mar. 5, 2010.

Jayaprakash et al., "Design and Synthesis of a PSMA Inhibitor-Doxorubicin Conjugate for Targeted Prostate Cancer Therapy," ChemMedChem 2006, 1, pp. 299-302.

Jeong et al., "Effect of cryoprotectants on the reconstitution of surfactant-free nanoparticles of poly(DL-lactide-co-glycolide)," *J. of Microencapsulation.* (2005) 22(6):593-601.

Jiang et al., "Preparation of PLA and PLGA Nanoparticles by Binary Organic Solvent Diffusion Method," *J. Cent. South Univ. Technol.* (2003) 10(3):202-206.

Koziara et al., "Blood Compatibility of Cetyl Alcohol/Polysorbate-Based Nanoparticles," *Pharma. Res.* (2005) 22(11):1821-1828.

Kozikowski et al., Design of Remarkably Simple, Yet Potent Urea-Based Inhibitors of Glutamate Carboxypeptidase II (NAALADase), *J. Med. Chem.* (2001) 44:298-301.

Kozikowski et al., "Synthesis of Urea-Based Inhibitors as Active Site Probes of Glutamate Carboxypeptidase II: Efficacy as Analgesic Agents," *J. Med. Chem.* (2004) 47:1729-1738.

Kwon, "Long Acting Porous Microparticle for Pulmonary Protein Delivery," *Int. J. Pharm.* (2007) 333:5-9.

Lyseng-Williamson et al., "Docetaxel a Review of its Use in Metastatic Breast Cancer," *Drugs.* (2005) 65(17):2513-16.

Maresca et al., "A Series of Halogenated Heterodimeric Inhibitors of Prostate Specific Membrane Antigen (PSMA) as Radiolabeled Probes for Targeting Prostate Cancer," *J. Med. Chem.* (2009) 52(2):347-57.

Majer et al., "Synthesis and Biological Evaluation of Thiol-Based Inhibitors of Glutamate Carboxypeptidase II: Discovery of an Orally Active GCP II Inhibitor," *J. Med. Chem.* (2003) 46:1989-1996.

Mease et al., "N-[N-[(S)-1,3-Dicarboxypropyl] Carbamoyl]-4-[18F] Fluorobenzyl-L-Cysteine, [18F] DCFBC: A New Imaging Probe for Prostate Cancer," *Clin. Cancer Res.* (2008) 14(10):3036-3043.

Misra et al., "Production of Multimeric Prostate-Specific Membrance Antigen Small-Molecule Radiotracers Using a Solid-Phase 99m Tc Preloading Strategy," *J. Nuclear Med.* (2007) 48(8):1379-1389.

Murugesan et al., "Pegylated Poly(lactide-co-glycolidel (PLGA) Nanoparticulate Delivery of Docetaxel: Synthesis of Diblock Copolymers, Optimization of Preparation Variables on Formulation Characteristics and in Vitro Release Studies." *J. Biomed. Nanotechnol.* (2007) 3:52-60.

Musumeci et al., "Lyoprotected Nanosphere Formulations for Paclitaxel Controlled Delivery." *J. Nanosci. Nanotech.* (2006) 6:3118-3125.

Musumeci et al., "PLA/PLGA Nanoparticles for Sustained Release of Docetaxel," *Int. J. Pharm.* (2006) 325:172-179.

Ojer, "Spray-Drying of Poly(anhydride) Nanoparticles for Drug/Antigen Delivery," *J. Drug Del. Sci. Tech.* (2010) 20(5):353-359.

Oliver et al., "Conformational and SAR Analysis of NAALADase and PSMA Inhibitors," *Biorg. Med. Chem.* (2003) 11:4455-4461.

Olivier, "Drug Transport to Brain with Targeted Nanoparticles," *The Journal of the American Society for Experimental NeuroTherapeutics.* (2005) 2:108-119.

Omelczuk et al., "The Influence of Polymer Glass Transition Temperature and Molecular Weight on Drug Release from Tablets Containing Poly(DL-lactic acid)." *Pharm. Res.* (1992) 9(1):26-32.

Peracchia et al., "PEG-coated nanaspheres from amphiphilic diblock and multiblock copolymers: Investigation of their drug encapsulation and release characteristics," *Journal of Controlled Release.* (1996) 46:223-231.

Pomper, Martin G., Russell H. Morgan Department of Radiology and Radiological Science, Johns Hopkins University, "New Developments in Molecular Imaging of Prostate Cancer," Topical Symposium on: Advanced Molecular Imaging Techniques in the Detection, Diagnosis, Therapy, and Follow-up of Prostate Cancer, Palazzo Barberini, Rome, Dec. 6, 2005.

Pourcelle, "PCL-PEG-based Nanoparticles Grafted with GRGDS Peptide: Preparation and Surface Analysis by XPS," *Biomacromolecules.* (2007) 8:3977-3983.

Pulkkinen et al., "Three-Step Tumor Targeting of Paclitaxel Using Biotinylated PLA-PEG Nanoparticles and Avidin-Biotin Technology: Formulation Development and in Vitro Anticancer Activity", *Eur. J. Pharm. Biopharm.* (2008) 70:66-74.

Riley et al., "Colloidal Stability and Drug Incorporation Aspects of Micellar-like PLA-PEG Nanoparticles," *Colloids Surf. B: Biointer.* (1999) 16:147-59.

Sapra et al., "Ligand-Targeted Liposomal Anticancer Drugs," *Prog. Lipid Res.* (2003) 42:439-462.

Senthilkumar et al., "Long Circulating PEGylated Poly(D,L-lactide-co-glycolide) Nanoparticulate Delivery of Docetaxel to Solid Tumors," *J. Drug Target.* (2008) 424-435.

Sweetman, "Martindale: The Complete Drug Reference," 33rd ed., 2002, Pharmaceutical Press, entry for Docetaxel, p. 534.

Tamilvanan et al., "Manufacturing Techniques and Excipients Used During the Design of Biodegradable Polymer-Based Microspheres Containing Therapeutic Peptide/Protein for Parenteral Controlled Drug Delivery," *J. Pharm. Sci. Tech.* (2008) 62(2):125-154.

Tang, Hailun, et al., "Prostate Targeting Ligands Based on N-Acetylated α-Linked Acidic Dipeptidase," *Biochem. Biophys. Res. Comm.* 307 (2003), pp. 8-14.

"Taxotere Dosage," [retrieved on Mar. 28, 2013]. http://www.drugs.com/dosage/taxotere.html.

Tobio et al., "Stealth PLA-PEG Nanoparticles as Protein Carriers for Nasal Administration," *Pharm. Res.* (1998) 15(2):270-275.

Vicari et al., "Paclitaxel Loading in PLGA Nanospheres Affected the in Vitro Drug Cell Accumulation and Antiproliferative Activity," *BMC Cancer.* (2008) 8:212.

Yamamoto et al., "Long-Circulating Poly(ethylene glycol)-poly(D,L-lactide) block copolymer micelles with Modulated Surface Charge," *Journal of Controlled Release.* (2001) 77:27-38.

(56) References Cited

OTHER PUBLICATIONS

Zhang et al., "Neointimal Hyperplasia Persists at Six Months after Siroli Mus-Eluting Stent Implantation in Diabetic Porcine," *Cardiovasc. Diabetol.* (2007) 6:16:1-7.

Zhou et al., "NAAG Peptidase Inhibitors and Their Potential for Diagnosis and Therapy," *Nature Rev. Drug Discov.* (2005) 4:1015-1026.

Altmann (Epothilone B and its analogs—a new family of anticancer agents, *Mini Rev Med Chem.* (2003) 3(2):149-158; Abstract Only [retrieved from Bentham Science, < URL: http://www.eurekaselect.com/80911/artcile>], 1 page.

Altmann (Epothilone B and its analogs—a new family of anticancer agents, *Mini Rev Med Chem.* (2003) 3(2):149-158; Abstract Only [retrieved from PUBMED, < URL: http://www.ncbi.nlm.nih.gov/pubmed/12570848>]), 1 page.

Dong et al., "In vitro and in vivo evaluation of methoxy polyethylene glycol-polylactide (MPEG-PLA) nanoparticles for small-molecule drug chemotherapy," (2007) *Biomaterials.* 28:4154-4160.

Extended European Search Report for EP 13162789.5 mailed Aug. 30, 2013, 7 pages.

Extended European Search Report for EP 13162786.1 mailed Aug. 30, 2013, 7 pages.

Eurasian Search Report for Application No. EA 201290497, dated Jan. 15, 2013.

Eurasian Official Action for EA 201170040, dated Jun. 29, 2012.

European Examination Report for EP 09794913.5, dated Jul. 16, 2012.

Extended European Search Report for EP 11186037.5, mailed Mar. 2, 2012.

Extended European Search Report for EP 09794913.5 mailed Jul. 4, 2013, 9 pages.

Extended European Search Report for EP 10842556.2 mailed Jul. 8, 2013, 9 pages.

Extended European Search Report for EP 10842557.0 mailed Jul. 8, 2013, 11 pages.

Extended European Search Report for EP 10842554.7 mailed Jul. 10, 2013, 9 pages.

Extended European Search Report for EP 09794917.6 mailed Aug. 7, 2013, 8 pages.

International Preliminary Report on Patentability for PCT/US2010/060575 dated Jun. 19, 2012, 11 pages.

Matsumoto et al., "Preparation of Nanoparticles consisted of poly(L-lactide)-poly(ethylene glycol)-poly(L-lactide) and Their Evaluation in Vitro," *International J. of Pharmaceutics.* (1999) 185:93-101.

Verrecchia et al., "Non-stealth (poly(lactic acid/albumin) ) and stealth (poly(lactic acid-polyethylene glycol) ) nanoparticles as injectable drug carriers," *J. of Controlled Release.* (1995) 36:49-61.

Dong et al., "(Methoxy poly(ethylene glycol)-poly(lactide) (MPEG-PLA) nanoparticles for controlled delivery of anticancer drugs," (2004) Biomaterials. 25:2843-2849.

Stolnik et al., "(Polylactide-poly(ethylene glycol) micellar-like particles as potential drug carriers: production, colloidal properties and biological performance," (2001) Journal Drug Targeting. 9:361-378.

Extended European Search Report for EP 11835279.8 mailed Feb. 28, 2014, 8 pages.

Gill et al., "Modulated Differential Scanning Calorimetry," *J. Thermal Analysis.* (1993) 40:931-939.

International Search Report for Application No. PCT/US2013/059936, dated Feb. 4, 2014 and mailed Feb. 4, 2014, 8 pages.

Merck (Betamethasone, Merck Index (Knovel, copyright 2006, 2012)), 3 pages.

LONG CIRCULATING NANOPARTICLES FOR SUSTAINED RELEASE OF THERAPEUTIC AGENTS

RELATED APPLICATIONS

This application is a continuation of U.S. Ser. No. 13/556,647, filed Jul. 24, 2012, which is a continuation of U.S. Ser. No. 12/638,297, filed Dec. 15, 2009, which claims priority to provisional applications U.S. Ser. No. 61/122,479, filed Dec. 15, 2008, U.S. Ser. No. 61/260,200, filed Nov. 11, 2009, and U.S. Ser. No. 61/249,022, filed Oct. 6, 2009, each of which is hereby incorporated by reference in its entirety.

STATEMENT REGARDING FEDERALLY SPONSORED RESEARCH OR DEVELOPMENT

This invention was made with United States Government support under Cooperative Agreement Number 70NANB7H7021 awarded by the National Institute of Standard and Technology (NIST). The United States Government has certain rights in the Invention.

BACKGROUND

Nanoparticles for the delivery of therapeutic agents have the potential to circumvent many challenges associated with traditional delivery approaches including lack of patient compliance to prescribed therapy, adverse effects, and inferior clinical efficacy due to lack of targeted delivery. Important technological advantages of nanoparticles for drug delivery include the ability to deliver water-insoluble and unstable drugs, incorporation of both hydrophobic and hydrophilic therapeutic agents, and ability to utilize various routes of administration. Nanoparticle delivery systems may also facilitate targeted drug delivery and controlled release applications, enhance drug bioavailability at the site of action, reduce dosing frequency, and minimize side effects.

Because of these possible advantages, nanoparticulate systems have been examined for use as drug delivery vehicles, including polymeric micelles, polymers, liposomes, low-density lipoproteins, dendrimers, hydrophilic drug-polymer complexes, and ceramic nanoparticles. Typical polymeric materials utilized in polymeric particulate drug delivery systems include polylactic acid (PLA), poly(D,L-glycolide) (PLG), and poly(lactide-co-glycolide) (PLGA). PLA and PLGA are listed as Generally Recognized as Safe (GRAS) under Sections 201(s) and 409 of the Federal Food, Drug, and Cosmetic Act, and are approved for use in commercially available microparticulate systems, including Decapeptyl®, Parlodel LA®, and Enantone Depot®, as well as in implant devices, such as Zoladex®.

However, certain nanoparticle systems, such as liposomes, are not amenable for use with certain therapeutic agents. Polymeric nanoparticles developed to date have limited effectiveness, in part because such nanoparticles clear from the body quickly once administered and/or may accumulate in healthy tissue where treatment is not needed. Control of delivery of an active agent, using nanosystems, remains a challenge.

Therefore there is a need for biocompatible compositions capable of extended delivery of active agents, e.g., anti-neoplastic agents, that provide for prolonged and/or increased plasma drug concentrations in a patient, especially as compared to administration of an active agent alone.

SUMMARY

In one aspect of the invention, a nanoparticle composition is provided that includes a biodegradable and/or biocompatible polymer and a therapeutic agent, wherein the biodegradable and/or biocompatible polymer matrix releases the therapeutic agent at a rate allowing controlled release of the agent over at least about 12 hours, or in some embodiments, at least about 24 hours For example, provided herein is a biocompatible nanoparticle composition comprising a plurality of long circulating nanoparticles, each comprising a biocompatible polymer and a therapeutic agent, said composition providing an elevated plasma concentration of the therapeutic agent for at least 12 hours when the composition is administered to a patient, and an area under the plasma concentration time curve (AUC) that is increased by at least 100% over the AUC provided when the therapeutic agent is administered alone to a patient.

In an embodiment, disclosed herein is a biocompatible nanoparticle composition comprising a plurality of long circulating nanoparticles, each comprising a α-hydroxy polyester-co-polyether and a therapeutic agent, said composition providing an elevated plasma concentration of the therapeutic agent for at least 6 hours, at least 12 hours, or at least 24 hours or more when the composition is administered to a patient, to provide an area under the plasma concentration time curve (AUC) that is increased by at least 100%, or at least by 150%, over the AUC provided when the therapeutic agent is administered alone to a patient.

In some embodiments, disclosed nanoparticles may provide an actual peak plasma concentration ($C_{max}$) that is at least 10% higher, or even at least 100% higher, as compared to a $C_{max}$ of said therapeutic agent when administered alone. Disclosed nanoparticles, for example, may provide a volume of distribution when administered to the patient that is less than or equal to about 5 plasma volumes. For example, disclosed nanoparticles and/or compositions may decrease the volume of distribution ($V_z$) by at least 50% as compared to the $V_z$ of the patient when the therapeutic agent is administered alone.

Disclosed biocompatible nanoparticle compositions may include long circulating nanoparticles that may further comprise a biocompatible polymer coupled to a targeting moiety, for example, a targeting moiety that is selected from the group consisting of a protein, peptide, antibody, antibody fragment, saccharide, carbohydrate, small molecule, glycan, cytokine, chemokine, nucleotide, lectin, lipid, receptor, steroid, neurotransmitter, cell surface marker, cancer antigen, or glycoprotein antigen. An exemplary targeting moiety may bind to prostate membrane specific antigen (PMSA). For example, a disclosed nanoparticle may include a biocompatible polymer coupled to a targeting moiety, e.g., a nanoparticle may include PLA-PEG-((S,S-2-{3-[1-carboxy-5-amino-pentyl]-ureido}-pentanedioic acid. Disclosed long circulating nanoparticles may include 1 to about 4% by weight, or 2% to about 4% by weight, of a biocompatible polymer coupled to a targeting moiety In some embodiments, a biocompatible nanoparticle may include a biocompatible polymer such as PLA-PEG. For example, a α-hydroxy polyester-co-polyether may be polylactic acid-co-polyethylene glycol, and/or a α-hydroxy polyester-co-polyether comprises about 16 kDa polylactic acid and about 5 kDa polyethylene glycol.

Disclosed long circulating nanoparticles may be about 80 to about 90 weight percent α-hydroxy polyester-co-polyether.

In some embodiments, disclosed long circulating nanoparticles may further comprise a biodegradable polymer, such as poly(lactic) acid. For example, long circulating nanoparticles may have about 40 to about 50 weight percent poly(lactic) acid, and about 40 to about 50 weight percent of α-hydroxy polyester-co-polyether. Compositions that include such biocompatible nanoparticles and a therapeutic agent may provide a peak plasma concentration ($C_{max}$) of a therapeutic agent at least 100% higher than the $C_{max}$ of the therapeutic agent when administered alone, and/or the area under the plasma concentration time curve (AUC) may increased by at least 200% over the AUC of the therapeutic agent when administered alone to the patient.

Disclosed nanoparticle compositions may include a therapeutic agent such as one selected from the group consisting of chemotherapeutic agents, diagnostic agents, prophylactic agents, nutraceutical agents, nucleic acids, proteins, peptides, lipids, carbohydrates, hormones, small molecules, metals, ceramics, drugs, vaccines, immunological agents, and combinations thereof, for example, a nanoparticle may include an anti-neoplastic agent such as docetaxel, vincristine, methotrexate, paclitaxel, or sirolimus. Disclosed nanoparticle compositions may further include an aqueous solution of a saccharide.

Also provided herein is a method of treating a solid tumor cancer, comprising administering disclosed nanoparticle composition to a patient (e.g. a mammal or primate) in need thereof. Such methods, may provide wherein at least 24 hours after administration, a solid tumor has significant concentration of therapeutic agent. Contemplated herein is a method of treating a solid tumor in a mammal in need thereof, comprising administering a nanoparticle composition comprising a plurality of nanoparticles each comprising a α-hydroxy polyester-co-polyether and a therapeutic agent, wherein the composition has an amount of therapeutic agent effective to inhibit the growth of said tumor, for example, a single dose of said composition may provide extended elevated plasma concentrations of said therapeutic agent in the patient for a least one day, (e.g. the peak plasma concentration ($C_{max}$) of the therapeutic agent after administration of the composition to the mammal is at least 10% higher than the $C_{max}$ of said therapeutic agent if administered in a non-nanoparticle formulation.)

Also provided herein is a method of minimizing unwanted side effects or toxicity of an active agent in a patient, comprising: administering a nanoparticle composition comprising a plurality of nanoparticles each comprising a α-hydroxy polyester-co-polyether and a therapeutic agent, wherein said composition is capable of delivery a higher plasma concentration of therapeutic agent to the patient as compared to administering the therapeutic agent alone, and wherein upon administering the nanoparticle composition the volume distribution of the active agent in the patient is reduced, as compared to the volume distribution if the therapeutic agent was administered alone. A method for modulating the plasma concentration of a therapeutic agent in a patient, e.g. a primate (e.g. human) is also provided, comprising: providing a polymeric nanoparticle comprising the therapeutic agent and administering the polymeric nanoparticle to the patient, thereby modulating the plasma concentration of the human patient. Disclosed therapeutic nanoparticles may include nanoparticles having a diameter of about 60 to about 120 nm, or about 70 to about 130 nm, or about 60 to about 140 nm, about 70 to about 140 nm, or about 50 to about 270 nm.

The invention may be more completely understood in consideration of the following detailed description of various embodiments of the invention in connection with the accompanying drawings.

DETAILED DESCRIPTION

Figure 1:
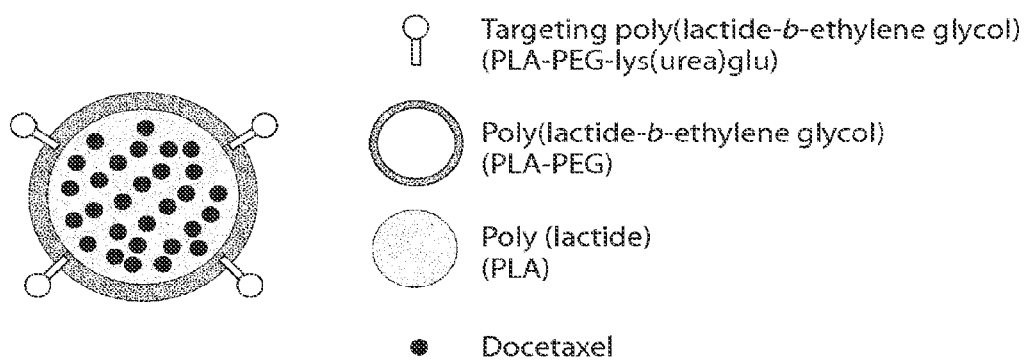
FIG. 1 is a schematic illustration of a nanoparticle according to one aspect of the present invention.

It is to be understood that the invention is not limited to the particular processes, compositions, or methodologies described, as these may vary. It is also to be understood that the terminology used in the description is for the purpose of describing particular versions or embodiments only and is not intended to limit the scope of the invention. All of the publications and references mentioned herein are incorporated by reference. Nothing herein is to be construed as an admission that the invention is not entitled to antedate such disclosure by virtue of prior invention.

As used herein the singular forms "a", "an" and "the" include plural reference unless the context clearly dictates otherwise. Further, unless defined otherwise, all technical and scientific terms used herein have the same meanings as commonly understood by one of ordinary skill in the art.

As used herein, the term "about" means plus or minus 10% of the numerical value of the number with which it is being used. Therefore, about 50% means in the range of 40%-60%.

An "effective amount" or "therapeutically effective amount" of a composition, as used herein, is a predetermined amount calculated to achieve a desired effect.

As used herein, the term "long-circulating" refers to enhanced stability in the circulatory system of a patient, regardless of biological activity.

As used herein, the prefix "nano" and the terms "nanophase" and "nanosize" refer to a special state of subdivision implying that a particle has an average dimension smaller than about 1000 nm ($1000 \times 10^{-9}$ m).

As used herein, the terms "poly(ethylene glycol)" or "PEG" and "poly(ethylene oxide)" or "PEO" denote polyethers comprising repeat —CH$_2$—CH$_2$—O— units. PEG and/or PEO can be different polymers depending upon end groups and molecular weights. As used herein, poly(ethylene glycol) and PEG describes either type of polymer.

An "α-hydroxy polyester" refers to polymers having monomers based on one or more α-hydroxy acid, such as poly(lactic) acid, poly(glycolic) acid, poly-lactic-co-glycolic acid, polycaprolactone.

The term "target", as used herein, refers to the cell type or tissue to which enhanced delivery of the therapeutic agent is desired. For example, diseased tissue may be a target for therapy.

As used herein, the term "therapeutic agent" means a compound utilized to image, impact, treat, combat, ameliorate, prevent or improve an unwanted condition or disease of a patient.

In an embodiment, disclosed long-circulating nanoparticles include a therapeutic agent and biodegradable and/or biocompatible polymeric particles, optionally functionalized with targeting moieties. The nanoparticles are designed to circulate in a vascular compartment of a patient for an extended period of time, distribute and accumulate at a target, and release the encapsulated therapeutic agent in a controlled manner. These characteristics can result in an increased level of therapeutic agent in the target and a potential reduction in off-target exposure. For example, the disclosed nanoparticles remain in circulation longer because, upon administration to a patient (e.g. a mammal, primate (e.g. human)), the disclosed nanoparticles are substantially confined to the vascular compartment of the patient, and are engineered to be cleared very slowly.

The activity of many therapeutic agents is dependent on their pharmacokinetic behavior. This pharmacokinetic behavior defines the drug concentrations and period of time over which cells are exposed to the drug. For most therapeutics, e.g. anti-neoplastics, longer exposure times are preferred as this results in increased killing of the cancer cells. In general, several parameters are used to describe drug pharmacokinetics. Peak plasma concentration, or maximum plasma concentration ($C_{max}$) and area under the curve (AUC) are examples. AUC is a measure of plasma drug levels over time and provides an indication of the total drug exposure. Generally, plasma concentration and plasma AUC for a therapeutic agent correlate with increased therapeutic efficacy.

The combination of long circulation time, confinement of particles to the vascular compartment and controlled release of drug results in higher circulating drug concentrations for longer periods of time (as evidenced by higher AUC and lower Vd). than drug alone, or, for example, drug in a PLA polymeric nanoparticles that does not include PLA-PEG, or that do not include e.g. PLA alone.

For example, provided herein, in an embodiment, is a biocompatible nanoparticle composition comprising a plurality of long circulating nanoparticles, each comprising a α-hydroxy polyester-co-polyether and a therapeutic agent. Such compositions may provide a therapeutic effect for at least 12 hours, at least 24 hours, or at least 36 hours, or 48 hours or more, upon administration to a patient. In some embodiments, peak plasma concentration ($C_{max}$) of the therapeutic agent of such nanoparticles, e.g. when the composition is administered to a patient, may be least 10% higher, 20% higher, or about 10% to about 100% higher, or more, than the $C_{max}$ of the same therapeutic agent when administered alone. Actual peak plasma concentration of delivered therapeutic agent includes both agent that is released from the nanoparticle (e.g. after administration) and therapeutic agent remaining in any nanoparticle remaining in the plasma, e.g. at a given time.

In another embodiment, disclosed nanoparticles may provide upon administration to a patient, an area under the plasma concentration time curve (AUC), that may be increased by at least 100%, at least 200%, or about 100% to about 500% or more, over the AUC of the therapeutic agent when administered alone to the patient. In another embodiment, a provided composition that includes disclosed nanoparticles may decrease the volume of distribution ($V_z$) of distributed active agent, upon administration, in a patient by at least 10%, or by at least 20%, or about 10% to about 100%, as compared to the $V_z$ of the patient when the therapeutic agent is administered alone. For example, a provided nanoparticle composition may provide $V_z$ in a patient that is on the same order of magnitude that the of plasma volume and/or a volume of distribution less than about 10 plasma volumes. For example, a disclosed nanoparticle composition may provide a Vz that is less than, or about, 2 times the plasma volume, or less than or about 8 plasma volumes. In an embodiment, a disclosed nanoparticle composition may provide a $V_z$ in a patient that is on about the same order of plasma volume, (e.g. about 5 L for an exemplary 70 kg patient), e.g. about a $V_z$ that indicates administered nanoparticles are substantially in the patient's plasma and not substantially in other tissues.

In some embodiments, disclosed nanoparticles may be used as a drug delivery vehicle based on the encapsulation of a therapeutic agent in a polymer matrix with controlled porosity and/or a soluble shell or matrix that upon dissolution releases the therapeutic agent in the immediate vicinity of the targeted area. The protection of the therapeutic agent provided by the polymer shell or matrix allows for the delivery of therapeutic agents that are water-insoluble or unstable. Furthermore, dissolution kinetics of the polymer can be designed to provide sustained release of therapeutic agents at a target for an extended period of time.

Disclosed nanoparticles can be used for a variety of applications, such as, without limitation, drug delivery, gene therapy, medical diagnosis, and for medical therapeutics for cancer, pathogen-borne diseases, hormone-related diseases, reaction-by-products associated with organ transplants, and other abnormal cell or tissue growth.

Provided herein, in an embodiment, are methods for treating a patient e.g. a mammal suffering from cancer, e.g. a solid tumor cancer, prostate cancer, breast cancer or lung cancer using e.g., disclosed nanoparticles. However, contemplated diseases that may be treated using disclosed nanoparticles include a broad range of diseases and find limitation only by e.g. the therapeutic agent, the availability of a marker and/or a targeting ligand for the disease.

In other embodiments, a nanoparticle delivery system is provided that mitigates against colloidal instability, agglomeration, polydispersity in nanoparticle size and shape, swelling, and leakage of encapsulated materials.

In yet another embodiment, nanoparticles for delivery of therapeutic agents are provided that exhibit encapsulation efficiency. Encapsulation efficiency is affected by factors including, for example, material characteristics of the polymer utilized as the carrier matrix, the chemical and physical properties of the therapeutic agent to be encapsulated, and type of solvents used in the nanoparticle fabrication process.

In yet another aspect, polymeric nanoparticles for delivery of therapeutic agents are provided that exhibit particle heterogeneity. Conventional polymeric nanoparticle fabrication techniques generally provide multimodal particle size distributions as a result of self-aggregation during nanoprecipitation of both the polymer and the drug molecules.

Polymeric nanoparticles for delivery of therapeutic agents are provided, in an embodiment, that may reduce or eliminate burst release effects. Conventional polymeric nanoparticle carriers frequently exhibit a bimodal drug release pattern with up to about 40-80% or more of the encapsulated drug released during the first several hours. After 24 to 48 hours, drug release is significantly reduced due to the increased diffusion barrier for drug molecules located deep within the polymer matrix. In such conventional nanoparticle carrier systems, poorly encapsulated drug molecules diffuse quickly into solution, which may lead to significant toxicity in vivo. Further, by the time the evacuated nanoparticles arrive and accumulate at the targeted site (e.g., tumor tissue), the nanoparticles generally have little or no remaining therapeutic efficacy.

In an embodiment, polymeric nanoparticles for delivery of therapeutic agents are provided that may evade rapid capture by the reticuloendothelial system (RES), leading to extended circulation time and elevated concentration of the nanoparticles in the blood. Rapid capture and elimination is typically caused by the process of opsonization in which opsonin proteins present in the blood serum quickly bind to conventional nanoparticles, allowing macrophages to easily recognize and remove these particulates before they can perform their designed therapeutic function. The extent and nature of opsonin adsorption at the surface of nanoparticles and their simultaneous blood clearance depend on the physicochemical properties of the particles, such as size, surface charge, and surface hydrophobicity. In yet another embodiment, a nanoparticle composition is provided including a biodegradable and/or biocompatible polymer matrix and a therapeutic agent coupled to the biodegradable and/or biocompatible polymer matrix wherein the clearance rate of said therapeutic agent coupled to the biodegradable and/or biocompatible polymer matrix is lower than the clearance rate of said therapeutic agent when administered alone.

In certain embodiments, methods are provided that mask or camouflage nanoparticles in order to evade uptake by the RES. One such method is the engineering of particles in which polyethers, such as poly(ethylene glycol) (PEG) or PEG containing surfactants, are deployed on the surface of nanoparticles. The presence of PEG and/or PEG-containing copolymers, e.g. on the surface of nanoparticles can result in an increase in the blood circulation half-life of the nanoparticles by several orders of magnitude. This method creates a hydrophilic protective layer around the nanoparticles that is able to repel the absorption of opsonin proteins via steric repulsion forces, thereby blocking and delaying the first step in the opsonization process.

FIG. 1 schematically illustrates a nanoparticle according to one aspect of the present invention. As shown in FIG. 1, docetaxel 100, an anti-neoplastic agent approved for the treatment of hormone refractory prostate cancer (HRPC), is encapsulated in a matrix 110 derived from the biodegradable and/or biocompatible polymers PLA and poly(lactide-b-ethylene glycol) (PLA-PEG). The polymer matrix 110 contains a targeting polymer (PLA-PEG-lys(urea)glu) 120 that is end-functionalized (through the 5 amino moiety) with the lysine-urea-glutamate heterodimer (S,S-2-{3-[1-carboxy-5-aminopentyl]-ureido}-pentanedioic acid (lys(urea)glu) 130, a small molecule ligand that selectively binds to PSMA, a clinically relevant prostate cancer cell surface marker.

Once the nanoparticles, e.g. as provided herein are administered, at least portions of the nanoparticle polymer(s) may be biologically degraded by, for example, enzymatic activity or cellular machinery into monomers and/or other moieties that cells can either use or excrete. In certain aspects of the invention, the dissolution or degradation rate of the nanoparticles is influenced by the composition of the polymer shell or matrix. For example, in some embodiments, the half-life of the polymer (the time at which 50% of the polymer is degraded into monomers and/or other nonpolymeric moieties) may be on the order of days, weeks, months, or years, depending on the polymer.

According to some aspects of the invention, nanoparticle delivery characteristics such as water uptake, controlled release of therapeutic agent, and polymer degradation kinetics may be optimized through selection of polymer shell or matrix composition.

Suitable polymers that may form some of the disclosed nanoparticles may include, but are not limited to, biodegradable α-hydroxy polyesters and biocompatible polyethers. In some aspects, exemplary polyesters include, for example, PLA, PLGA, PEG, PEO, PEGylated polymers and copolymers of lactide and glycolide (e.g., PEGylated PLA, PEGylated PGA, PEGylated PLGA), and derivatives thereof. In other aspects, suitable polymers include, for example, polyanhydrides, poly(ortho ester) PEGylated poly(ortho ester), poly(caprolactone), PEGylated poly(caprolactone), polylysine, PEGylated polylysine, poly(ethylene inline), PEGylated poly(ethylene imine), poly(L-lactide-co-L-lysine), poly (serine ester), poly(4-hydroxy-L-proline ester), poly[a-(4-aminobutyl)-L-glycolic acid], and combinations and derivatives thereof.

In other aspects, a polymer matrix may comprise one or more acrylic polymers. Exemplary acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly (methacrylic acid polyacrylamide) copolymer, aminoalkyl methacrylate copolymer, glycidyl methacrylate copolymers, polycyanoacrylates, and combinations thereof. The matrix may include dextran, acylated dextran, chitosan (e.g., acetylated to various levels), poly(vinyl) alcohol (for example, hydrolyzed to various degrees), and/or alginate, e.g. alginate complexed to bivalent cations such as a calcium alginate complex.

Nanoparticles disclosed herein include one, two, three or more biocompatible and/or biodegradable polymers. For example, a contemplated nanoparticle may include about 10 to about 99 weight percent of one or more block co-polymers that include a biodegradable polymer and polyethylene glycol, and about 0 to about 50 weight percent of a biodegradable homopolymer. Exemplary therapeutic nanoparticles may include about 40 to about 90 weight percent poly(lactic) acid-poly(ethylene)glycol copolymer or about 40 to about 80 weight percent poly(lactic) acid-poly(ethylene)glycol copolymer. Such poly(lactic) acid-block-poly(ethylene)glycol copolymer may include poly(lactic acid) having a number average molecular weight of about 15 to 20 kDa (or for example about 15 to about 100 kDa, e.g., about 15 to about 80 kDa), and poly(ethylene)glycol having a number average molecular weight of about 2 to about 10 kDa, for example, about 4 to about 6 kDa. For example, a disclosed therapeutic nanoparticle may include about 70 to about 90 weight percent PLA-PEG and about 5 to about 25 weight percent active agent (e.g. docetaxel), or about 30 to about 50 weight percent PLA-PEG, about 30 to about 50 weight percent PLA or PLGA, and about 5 to about 25 weight percent active agent (e.g. docetaxel). Such PLA ((poly)lactic acid) may have a number average molecular weight of about 5 to about 10 kDa. Such PLGA (poly lactic-co-glycolic acid) may have a number average molecular weight of about 8 to about 12 kDa. It should be appreciated that disclosed PLA-PEG copolymers may include a chemical linker, oligomer, or polymer chain between the PLA and PEG blocks, e.g., may include PLA-linker-PEG.

For example, disclosed nanoparticles may include about 10 to 15 weight percent active agent (e.g. about 10 weight percent docetaxel), and about 86 to about 90 weight percent PLA-PEG (with e.g. PLA about 16 kDa and PEG about 5 kDa, e.g. about 87.5% PLA-PEG (16 kDa/5 kDa)), and optionally e.g. a PLA-PEG-lys(urea)-glu (e.g. at 2.5 weight percent).

Alternatively, a disclosed nanoparticle, which may have slow release properties, may include about 42 to about 45 weight percent PLA-PEG (with e.g. PLA about 16 kDa and PEG about 5 kDa), (e.g. 43.25% PLA-PEG), about 42 to 45 weight percent PLA (e.g. about 75 kDa) (e.g. 43.25% PLA/75 kDa) and about 10 to 15 weight percent active agent (e.g. docetaxel). For example, disclosed nanoparticles may optionally include about 1 to about 50 weight percent poly(lactic) acid or poly(lactic) acid-co-poly (glycolic) acid (which does not include PEG, e.g a homopolymer of PLA), or may optionally include about 1 to about 50 weight percent, or about 10 to about 50 weight percent or about 30 to about 50 weight percent poly(lactic) acid or poly(lactic) acid-co-poly (glycolic) acid. In an embodiment, disclosed nanoparticles may include two polymers, e.g. PLA-PEG and PLA, in a weight ratio of about 30:60 to about 60:30, e.g, about 40:60, about 60:40, or about 50:50.

Such substantially homopolymeric poly(lactic) or poly(lactic)-co-poly(glycolic) acid may have a weight average molecular weight of about 10 to about 130 kDa, for example, about 20 to about 30 kDa, or about 100 to about 130 kDa. Such homopolymeric PLA may have a number average molecule weight of about 5 to about 90 kDa, or about 5 to about 12 kDa, about 15 to about 30 kDa, or about 60 to about 90 kDa. Exemplary homopolymeric PLA may have a number average molecular weight of about 80 kDa or a weight average molecular weight of about 124 kDa. As is known in the art, molecular weight of polymers can be related to an inherent viscosity. In some embodiments, homopolymer PLA may have an inherent viscosity of about 0.2 to about 0.4, e.g. about 0.3; in other embodiments, PLA may have an inherent viscosity of about 0.6 to about 0.8. Exemplary PLGA may have a number average molecular weight of about 8 to about 12 kDa.

In other embodiments, modified surface chemistry and/or small particle size of disclosed nanoparticles may contribute to the effectiveness of the nanoparticles in the delivery of a therapeutic agent. For example, in one disclosed aspect, nanoparticle surface charge may be modified to achieve slow biodegradation and reduce clearance of the nanoparticles. In another aspect, porosity of the polymer shell or matrix is optimized to achieve extended and controlled release of the therapeutic agent. For example, in one embodiment of the invention, the nanoparticles may have porosity in the range of about 10 to about 90 percent and/or a pore diameters in the range of about 0.001 to about 0.01 microns. Further, without wishing to be bound by theory, because of their small size and persistence in the circulation, the nanoparticles according to some embodiments of the invention may be able to penetrate the altered and often compromised vasculature of tumors via the enhanced permeability and retention (EPR) effect resulting in preferential accumulation of nanoparticles in tumor interstitium.

Examples of therapeutic agents that may form part of the disclosed nanoparticles include, but are not limited to, chemotherapeutic agents (e.g. anti-cancer agents), diagnostic agents (e.g. contrast agents, radionuclides, and fluorescent, luminescent, and magnetic moieties), prophylactic agents (e.g. vaccines), nutraceutical agents (e.g. vitamins and minerals), nucleic acids (e.g., siRNA, RNAi, and mircoRNA agents), proteins (e.g. antibodies), peptides, lipids, carbohydrates, hormones, small molecules, metals, ceramics, drugs, vaccines, immunological agents, and/or combinations thereof. For example, the active agent or drug may be a therapeutic agent such as an antineoplastic such as a mTor inhibitor (e.g., sirolimus (rapamycin), temsirolimus, or everolimus), vinca alkaloids such as vincristine, a diterpene derivative, a taxane such as paclitaxel (or its derivatives such as DHA-paclitaxel or PG-paxlitaxel), docetaxel, or methatrexate.

In some aspects of the invention, the therapeutic agent to be delivered is an agent useful in the treatment of cancer (e.g., a solid tumor cancer e.g., prostate or breast cancer). Such therapeutic agents may include, for example, doxorubicin (adriamycin), gemcitabine (gemzar), daunorubicin, procarbazine, mitomycin, cytarabine, etoposide, methotrexate, 5-fluorouracil (5-FU), vinblastine, vincristine, bleomycin, paclitaxel (taxol), docetaxel (taxotere), mitoxantrone, mitoxantrone hydrochloride, aldesleukin, asparaginase, busulfan, carboplatin, cladribine, camptothecin, CPT-Il, lO-hydroxy-7-ethyl-camptothecin (SN38), dacarbazine, S-I capecitabine, ftorafur, 5'deoxyfluorouridine, UFT, eniluracil, deoxycytidine, 5-azacytosine, 5-azadeoxycytosine, allopurinol, 2-chloroadenosine, trimetrexate, aminopterin, methylene-10-deazaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab and combinations thereof.

In some embodiments, contemplated nanoparticles may include more than one therapeutic agent. Such nanoparticles may be useful, for example, in aspects where it is desirable to monitor a targeting moiety as such moiety directs a nanoparticle containing a drug to a particular target in a subject.

Figure 2:
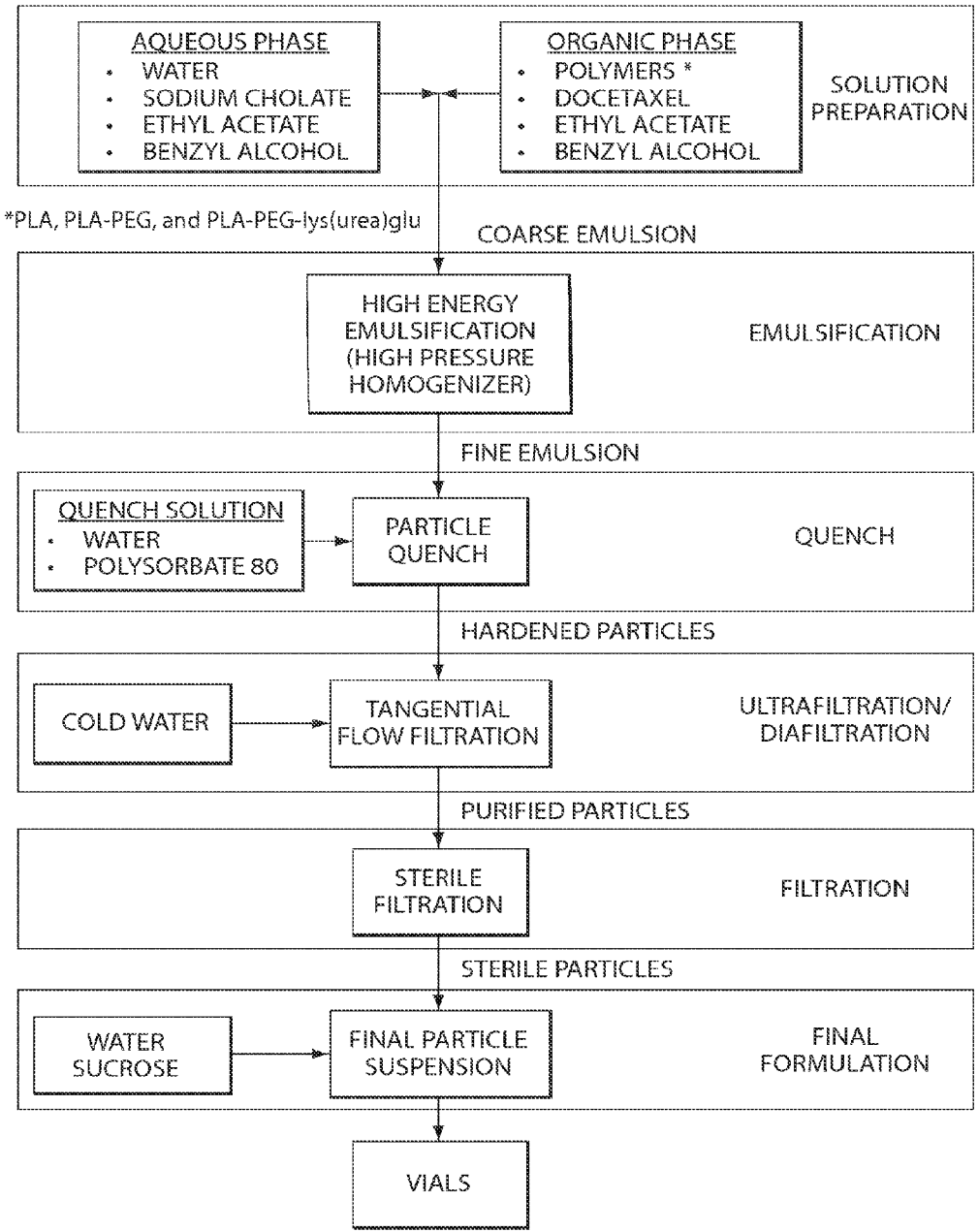
FIG. 2 is a block diagram of the emulsion process used in the fabrication of nanoparticles in one aspect of the present invention.

Disclosed nanoparticles may be formed using an emulsion process, e.g. as presented as a block diagram in FIG. 2. As shown in FIG. 2, an organic polymer/drug solution containing docetaxel, PLA, PLA-PEG, and PLA-PEG-lys(urea)glu dissolved in a co-solvent mixture of ethyl acetate and benzyl alcohol is dispersed in an aqueous solution of sodium cholate, ethyl acetate, and benzyl alcohol to form a coarse emulsion. In some aspects the conditions under which the emulsion process is performed favor the orientation of the PEG and/or PEG-lys(urea)glu polymer chains toward the particle surface. In other aspects, an orientation is achieved where the PEG is folded within the nanoparticle polymer shell or matrix.

As presented in FIG. 2, a coarse emulsion can be passed through a high pressure homogenizer to reduce the droplet size, forming a fine emulsion. The fine emulsion is diluted into an excess volume of a quench solution of cold water containing polysorbate 80. The presence of polysorbate 80 serves to remove excess therapeutic agent that has not been encapsulated in the nanoparticle. In some aspects of the present invention, polysorbate 80 may also be adhered or associated with a nanoparticle surfaces. While not wishing to be bound by theory, polysorbate 80 coupled to the nanoparticle surfaces may impact characteristics such as controlled release of therapeutic agent and polymer degradation kinetics. Quenching may be performed at least partially at a temperature of about 5° C. or less. For example, water used in the quenching may be at a temperature that is less that room temperature (e.g., about 0 to about 10° C., or about 0 to about 5° C.).

In some embodiments, not all of the therapeutic agent (e.g., docetaxel) is encapsulated in the particles at this stage, and a drug solubilizer is added to the quenched phase to form a solubilized phase. The drug solubilizer may be for example, Tween 80, Tween 20, polyvinyl pyrrolidone, cyclodextran, sodium dodecyl sulfate, or sodium cholate. For example, Tween-80 may added to the quenched nanoparticle suspension to solubilize the free drug and prevent the formation of drug crystals. In some embodiments, a ratio of drug solubilizer to therapeutic agent (e.g., docetaxel) is about 100:1 to about 10:1.

Ethyl acetate and benzyl alcohol are extracted from the organic phase droplets, resulting in formation of a hardened nanoparticle suspension. For example, docetaxel or other active agent may be encapsulated at e.g. a loading level of 10% w/w; corresponding to more than 10,000 drug molecules per nanoparticle.

The nanoparticle suspension is processed using tangential flow ultrafiltration/diafiltration (UF/DF) with cold water to remove processing aids and to concentrate the nanoparticles to a desired value. Residual precursor materials and excess organics present in unwashed nanoparticle suspensions may have a detrimental impact on biomedical applications as well as undesired toxic effects on the physiological system. The washed nanoparticle suspension is then passed through a prefilter and at least two sterilizing-grade filters.

Once the nanoparticles have been prepared, they may be combined with an acceptable carrier to produce a pharmaceutical formulation, according to another aspect of the invention. As would be appreciated by one of skill in this art, the carrier may be selected based on factors including, but not limited to, the route of administration, the location of the targeted disease tissue, the therapeutic agent being delivered, and/or the time course of delivery of the therapeutic agent. For example, as shown in FIG. 2, a concentrated sucrose solution is aseptically added to the sterile nanoparticle suspension to produce a pharmaceutical formulation. The sucrose serves as a cryoprotectant and a tonicity agent. In this embodiment, the resulting pharmaceutical formulation is a sterile, aqueous, injectable suspension of docetaxel encapsulated in nanoparticles comprised of biocompatible and biodegradable polymers. The suspension is assayed for docetaxel content, and may be aseptically diluted to the desired concentration. In some embodiments, the particle suspension is aseptically filled and sealed in glass vials. In other embodiments, the bulk drug product suspension is stored frozen at −20° C.±5° C. prior to filling into vials.

The fabrication methods for the nanoparticles of the invention may be modified in some embodiments to achieve desired drug-delivery features. For example, nanoparticle characteristics such as surface functionality, surface charge, particle size, zeta (ζ) potential, hydrophobicity, controlled release capability, and ability to control immunogenicity, and the like, may be optimized for the effective delivery of a variety of therapeutic agents. Furthermore, the long-circulating nanoparticles produced according to the emulsion process shown in FIG. 2 are well dispersed and unagglomerated, which facilitates conjugation or functionalization of the nanoparticle surfaces with targeting moieties.

Disclosed nanoparticles may include optional targeting moieties, which may be selected to ensure that the nanoparticles selectively attach to, or otherwise associate with, a selected marker or target. For example, in some embodiments, disclosed nanoparticles may be functionalized with an amount of targeting moiety effective for the treatment of prostate cancer in a subject (e.g., a low-molecular weight PSMA ligand). Through functionalization of nanoparticle surfaces with such targeting moieties, the nanoparticles are effective only at targeted sites, which minimizes adverse side effects and improves efficacy. Targeted delivery also allows for the administration of a lower dose of therapeutic agent, which may reduce undesirable side effects commonly associated with traditional treatments of disease.

In certain aspects, disclosed nanoparticles may be optimized with a specific density of targeting moities on the nanoparticle surface, such that e.g., an effective amount of targeting moiety is associated with the nanoparticle for delivery of a therapeutic agent. For example, the fraction of the biodegradable and/or biocompatible polymer matrix functionalized with a targeting moiety may be less than 80% of the total. According to another embodiment, the fraction of the biodegradable and/or biocompatible polymer matrix functionalized with a targeting moiety is less than about 50% of the total. Increased density of the targeting moiety may, in some embodiments, increase target binding (cell binding/target uptake).

Exemplary targeting moieties include, for example, proteins, peptides, antibodies, antibody fragments, saccharides, carbohydrates, glycans, cytokines, chemokines, nucleotides, lectins, lipids, receptors, steroids, neurotransmitters and combinations thereof. The choice of a marker may vary depending on the selected target, but in general, markers that may be useful in embodiments of the invention include, but are not limited to, cell surface markers, a cancer antigen (CA), a glycoprotein antigen, a melanoma associated antigen (MAA), a proteolytic enzyme, an angiogenesis marker, a prostate membrane specific antigen (PMSA), a small cell lung carcinoma antigen (SCLCA), a hormone receptor, a tumor suppressor gene antigen, a cell cycle regulator antigen, a proliferation marker, and a human carcinoma antigen. Exemplary targeting moieties include:

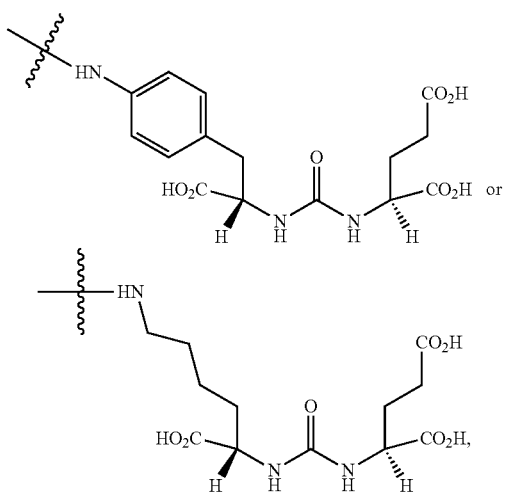

-lys-(urea)glu, which may be conjugated to PEG, e.g. a disclosed nanoparticle may include PLA-PEG-targeting moiety, e.g. S,S-2-{3-[1-carboxy-5-amino-pentyl]-ureido}-pentanedioic acid. For example, disclosed nanoparticles may include about 10 to 15 weight percent active agent (e.g. docetaxel), and about 86 to about 90 weight percent PLA-PEG (with e.g. PLA about 16 kDa and PEG about 5 kDa), and about 2 to about 3 weight percent PLA-PEG-lys(urea)glu (16 kDa/5 kDa PLA-PEG). Alternatively, a disclosed nanoparticle may include about 42 to about 45 weight percent PLA-PEG (with e.g. PLA about 16 kDa and PEG about 5 kDa) about 42 to 45 weight percent PLA (e.g. about 75 kDa), about 10 to 15 weight percent active agent (e.g. docetaxel), and about 2 to about 3 weight percent PLA-PEG-lys(urea)glu (16/5 PLA-PEG).

In other aspects of the invention, targeting moieties are targeted to an antigen associated with a disease of a patient's immune system or a pathogen-borne condition. In yet another aspect, targeting moieties are targeted to cells present in normal healthy conditions. Such targeting moieties may be directly targeted to a molecule or other target or indirectly targeted to a molecule or other target associated with a biological molecular pathway related to a condition.

The amount of nanoparticles administered to a patient may vary and may depend on the size, age, and health of the patient, the therapeutic agent to be delivered, the disease being treated, and the location of diseased tissue. Moreover, the dosage may vary depending on the mode of administration.

Various routes of administration are contemplated herein. In a particular aspect, the nanoparticles are administered to a subject systemically. Further, in some aspects, methods of administration may include, but are not limited to, intravascular injection, intravenous injection, intraperitoneal injection, subcutaneous injection, and intramuscular injection. According to aspects of the present invention, the nanoparticles necessitate only a single or very few treatment sessions to provide effective treatment of disease, which ultimately may facilitate patient compliance. For example, in some aspects, administration of the nanoparticles can occur via intravenous infusion once every three weeks.

Also contemplated herein are methods of treating solid tumors, e.g. prostate, lung, breast or other cancers, comprising administering a disclosed nanoparticle composition to a patient, e.g. a mammal in need thereof. For example, after such administration, e.g. at least after 12 hours, 24 hours, 36 hours, or 48 hours, or more after administration, the solid tumor may have significant concentration of therapeutic agent, e.g. may have an increase in tumor drug concentration of at least about 20%, or at least about 30% or more active agent (e.g. docetaxel) as compared to the amount present in a tumor after administration of (e.g. the same dosage) of therapeutic agent alone (e.g. not in a disclosed nanoparticle composition).

Disclosed herein is a method of treating a solid tumor in a mammal comprising administering a nanoparticle composition comprising a plurality of nanoparticles each comprising a α-hydroxy polyester-co-polyether and a therapeutic agent, wherein the composition has an amount of therapeutic agent effective to inhibit the growth of said tumor, for example, wherein single dose of said composition provides extended release of said therapeutic agent for a least one day. Such methods may provide an actual peak plasma concentration ($C_{max}$) of the therapeutic agent after administration of the composition to the mammal that is at least 10% higher, or at least 20% higher or 100% higher or more than the $C_{max}$ of said therapeutic agent if administered in a non-nanoparticle formulation. Disclosed methods may provide, upon administration of nanoparticles, an area under the plasma concentration time curve (AUC) in a patient that is increased by at least 100% over the AUC provided when the therapeutic agent is administered alone to a patient. In some embodiments, disclosed methods may also, alone or in addition to the above plasma parameters, decrease the volume of distribution ($V_z$) of the therapeutic agent upon administration by at least 50% as compared to the $V_z$ of the patient when the therapeutic agent is administered alone.

A method of minimizing unwanted side effects or toxicity of an active or therapeutic agent in a patient is also provided herein. For example, disclosed nanoparticles, may, upon administration, provide a higher plasma concentration of therapeutic agent as compared to administering an equivalent dosage of therapeutic agent alone. However, upon administration, in some embodiments, disclosed nanoparticles circulate substantially in the vascular compartment, and therefore may not contribute significantly to other areas that may cause toxicity or unwanted side effects.

In order that the invention disclosed herein may be more efficiently understood, examples are provided below. It should be understood that these examples are for illustrative purposes only and are not to be construed as limiting the invention in any manner.

EXAMPLES

Example 1

In Vitro Release of Docetaxel from Nanoparticles

A suspension of docetaxel encapsulated in nanoparticles fabricated according to the emulsion process depicted in FIG. 2 and Example 12 using 87.5 weight percent PLA-PEG, 10 wt. % docetaxel, and 2.5 wt. percent docetaxel (Formulation A) (all docetaxel nanoparticle formulations used in these Examples were in a composition of 5% nanoparticles, 65% water, and 30% sucrose). was placed in a dialysis cassette and incubated in a reservoir of phosphate buffered saline (PBS) at 37° C. with stirring. Samples of the dialysate were collected and analyzed for docetaxel using reversed phase high performance liquid chromatography (HPLC). For comparison, conventional docetaxel was analyzed under the same procedure.

Figure 3:
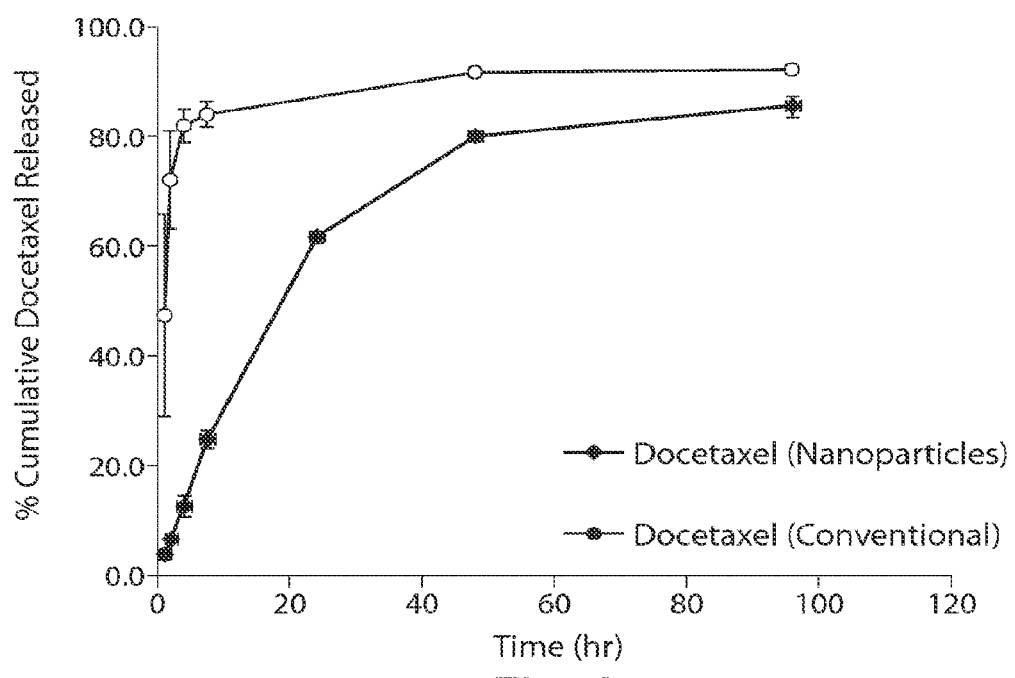
FIG. 3 depicts the in vitro release of docetaxel from nanoparticles and conventional docetaxel.

FIG. 3 presents the in vitro release profile of docetaxel encapsulated in nanoparticles compared to conventional docetaxel. Release of the encapsulated docetaxel from the polymer matrix was essentially linear over the first 24 hours with the remainder gradually released over a period of about 96 hours.

Example 2

Single Dose Pharmacokinetic Study of Docetaxel Encapsulated in Nanoparticles and Conventional Docetaxel in Sprague-Dawley Rats Six- to eight-week old male Sprague-Dawley rats were administered a single bolus dose (5 mg/kg of docetaxel) of docetaxel encapsulated in nanoparticles or conventional docetaxel via a tail vein. The dose groups consisted of six rats each. Blood was drawn at 0.083, 0.5, 1, 2, 3, 4, 6, and 24 hours post-dosing and processed to plasma. The concentration of total docetaxel in plasma was measured by a liquid chromatography-mass spectrometry (LC-MS) method following extraction with methyl tert-butyl ether (MTBE). The MTBE extraction does not differentiate nanoparticle-encapsulated docetaxel from docetaxel that was released from the nanoparticles into the plasma, and as such, the LC-MS data does not distinguish between the two.

Figure 4:
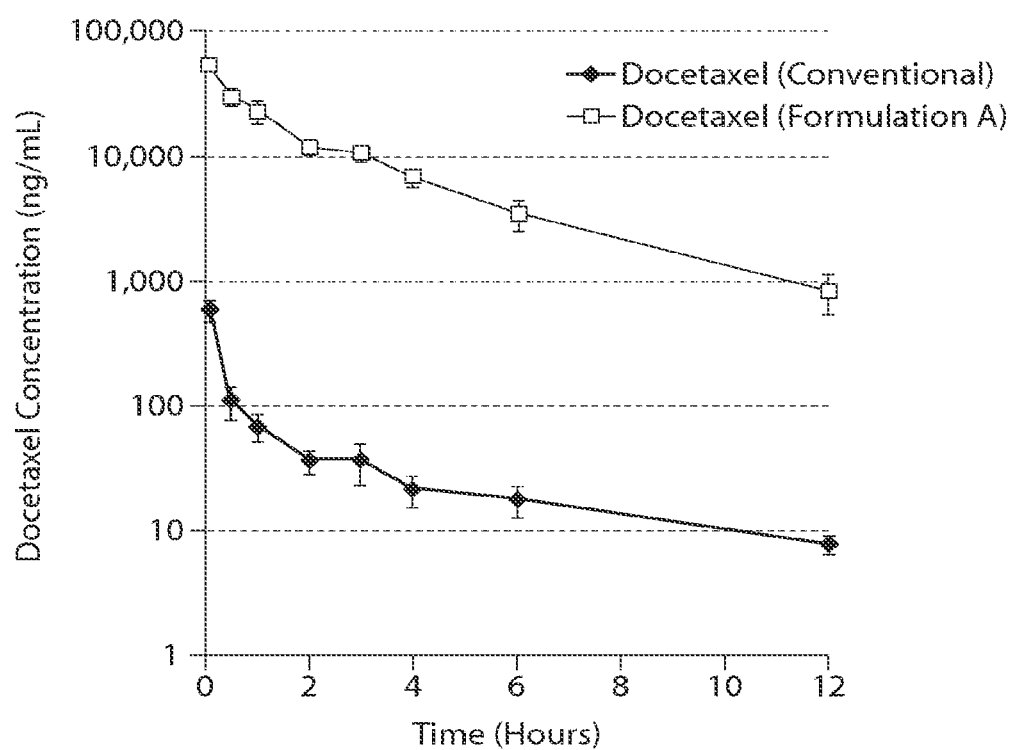
FIG. 4 depicts the pharmacokinetics of docetaxel encapsulated in nanoparticles and conventional docetaxel in rats.

FIG. 4 and Example Table 2.1 present the observed pharmacokinetic profiles and pharmacokinetic parameters, respectively, of docetaxel encapsulated in nanoparticles and conventional docetaxel. Example Table 2.1 further includes data from the preclinical development of TAXOTERE® for comparative reference (Bissery et al. 1995). The results for conventional docetaxel were consistent with those reported in literature (Bissery et al. 1995), indicating docetaxel was rapidly cleared from the blood and distributed to tissues. The peak plasma concentration ($C_{max}$) was observed at the first sampling time point for all treatments.

The $C_{max}$ and AUC of the docetaxel encapsulated in nanoparticles were approximately 100 times higher than that for conventional docetaxel. The difference in the $C_{max}$ may be attributable to having missed the rapid initial tissue distribution phase for conventional docetaxel. The data indicate that the docetaxel encapsulated in nanoparticles largely remains in circulation upon injection and is slowly cleared over a 24 hour period. The data further shows that docetaxel is released from the nanoparticles in a controlled manner during the 24 hour period (e.g., rapid burst release is not observed). If the nanoparticles were very quickly cleared from circulation, the large increase in AUC would not be observed. Similarly, if there was rapid burst release of docetaxel from the nanoparticles, the pharmacokinetic profile would be expected to more closely resemble that of conventional docetaxel.

an approximate 2-fold decrease in plasma concentration over the 24 hour period studied. These results are indicative of limited or delayed nanoparticle clearance via the mononuclear phagocyte system (MPS) relative to that often observed for particulate formulations. Without wishing to be bound by theory, this difference in plasma clearance times may be attributed to certain nanoparticle characteristics, including particle size and surface properties (e.g., surface charge and porosity).

The distinctions in plasma profiles of docetaxel encapsulated in nanoparticles and conventional docetaxel indicate that encapsulation of docetaxel in the nanoparticles prevents it from being rapidly distributed from the plasma compartment, resulting in significantly higher $C_{max}$ and AUC values relative to conventional docetaxel.

The differences in the profiles of docetaxel encapsulated in nanoparticles wherein the ligand of the PLA-PEG-lys(urea)glu targeting polymer was $^{14}C$-labeled and the docetaxel encapsulated in nanoparticles wherein the encapsulated docetaxel was $^{14}C$-labeled are reflective of the controlled release of docetaxel from the polymeric matrix of the nanoparticles. If docetaxel was released very quickly from the nanoparticles, it would be expected to be rapidly distributed from the plasma, yielding a profile similar to that of conventional docetaxel. Conversely, if docetaxel was retained in the nanoparticles over this timeframe, the profiles of the docetaxel encapsulated in nanoparticles wherein the ligand of the PLA-PEG-lys(urea)glu targeting polymer was $^{14}C$-labeled and the

EXAMPLE TABLE 2.1

Summary of Docetaxel Encapsulated in Nanoparticles and Conventional Docetaxel Pharmacokinetic Parameters

|  | Species | Dose (mg/kg) | $t_{max}^{a}$ (min) | $C_{max}$ (ng/mL) | $t_{1/2}$ (h) | $AUC_{0-\infty}$ (ng/mL · h) | CL (L/h/kg) |
|---|---|---|---|---|---|---|---|
| Conventional Docetaxel (Bissery et al. 1995) | Sprague-Dawley Rats | 5 | 2 | 4,100 | $0.8^{b}$ | 910 | 5.5 |
| Conventional Docetaxel | Sprague-Dawley Rats | 5 | 5 | 600 | $4.4^{c}$ | 623 | 2.33 |
| Docetaxel Encapsulated in Nanoparticles | Sprague-Dawley Rats | 5 | 5 | 54,800 | $2.6^{c}$ | 57,300 | 0.01 |

[a]For each treatment, $t_{max}$ equals the first sampling time.
[b]The study duration was 6 hours.
[c]The half life was determined from 2-12 hours.

Example 3

Tissue Distribution Study of Docetaxel Encapsulated in Nanoparticles and Conventional Docetaxel in Sprague-Dawley Rats Six- to eight-week old male Sprague-Dawley rats were administered a single bolus intravenous dose of one of the following: (1) docetaxel encapsulated in nanoparticles in which the ligand of the PLA-PEG-lys(urea)glu targeting polymer was $^{14}C$-labeled, (2) docetaxel encapsulated in nanoparticles in which the encapsulated docetaxel was $^{14}C$-labeled, (3) $^{14}C$-labeled conventional docetaxel.

Blood was drawn at 1, 3, 6, 12, and 24 hours post-dosing and processed to plasma. Immediately following blood collection, the rats were euthanized by $CO_2$ asphyxiation and tissues were immediately collected, blotted, weighed, and frozen on dry ice. Tissue samples were stored frozen (approximately –70° C.) until analysis for radioactivity by liquid scintillation (LS) counting.

Figure 5:
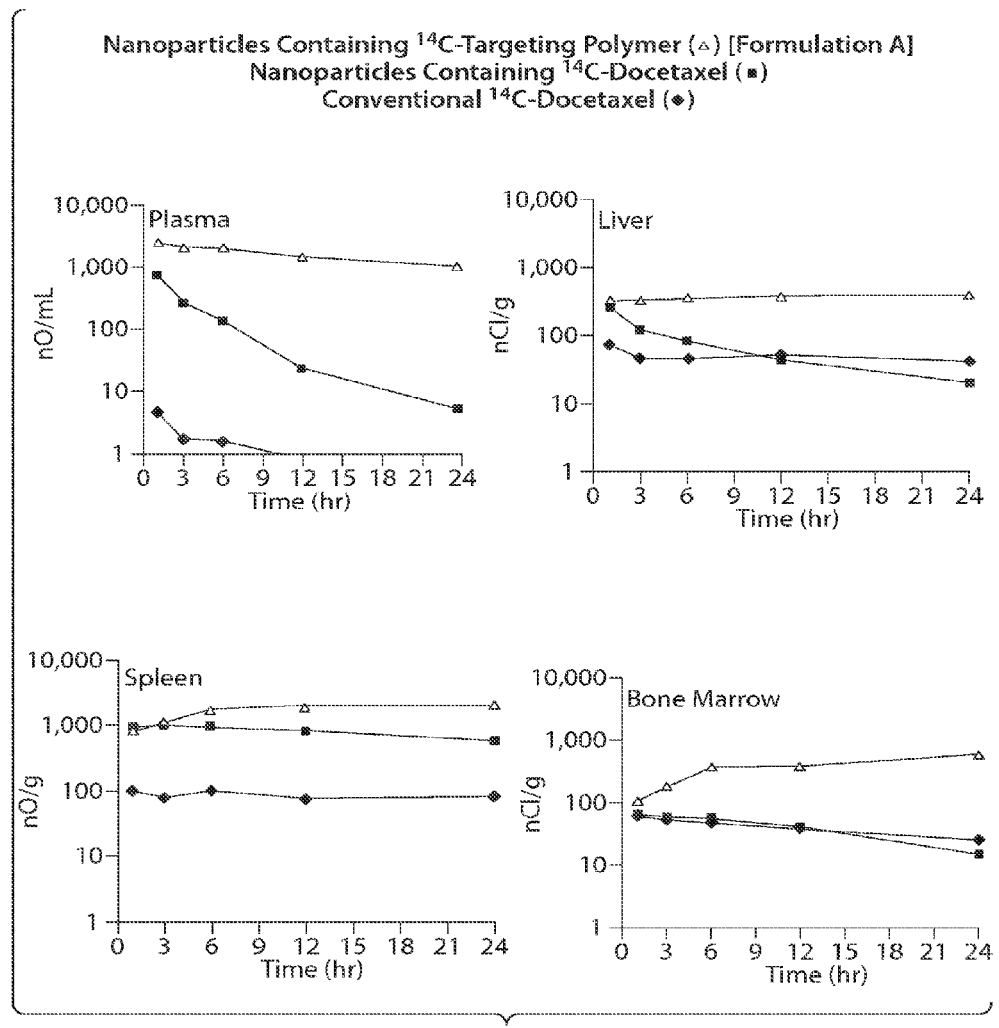
FIG. 5 depicts the distribution of radioactivity determined in selected tissues of rats after IV administration of nanoparticles containing $^{14}$C-targeting polymer (▲) nanoparticles containing $^{14}$C-docetaxel (■), and conventional $^{14}$C-docetaxel (♦).

As shown in FIG. 5, the docetaxel encapsulated in nanoparticles was gradually cleared from the plasma, exhibiting docetaxel encapsulated in nanoparticles wherein the encapsulated docetaxel was $^{14}C$-labeled would be superimposable.

Example Tables 3.1, 3.2, and 3.3 present the tissue distribution of radioactivity determined in rats after intravenous (IV) administration of (1) docetaxel encapsulated in nanoparticles in which the ligand of the PLA-PEG-lys(urea)glu targeting polymer was $^{14}C$-labeled, (2) docetaxel encapsulated in nanoparticles in which the encapsulated docetaxel was $^{14}C$-labeled, and (3) $^{14}C$-labeled conventional docetaxel, respectively. Example FIG. 5 contains the radioactivity concentration curves of the test articles determined in plasma, liver, spleen, and bone marrow.

Lower levels of nanoparticles (i.e., radioactivity from the $^{14}C$-labeled targeting polymer) were detected in all tissues relative to plasma except in the spleen, where nanoparticle concentrations were higher than plasma at 12 and 24 hours. It cannot be determined to what extent the radioactivity in tissues reflect the content in blood contained within the tissues versus the tissues themselves, because the tissues were not exsanguinated.

At time points closely following administration, the concentration of docetaxel encapsulated in nanoparticles was higher in most tissues than conventional docetaxel. After 24 hours, the concentration of docetaxel derived from the nanoparticles was lower than or approximately the same as the concentration of conventional docetaxel in all of the tissues evaluated, except the spleen.

Although the concentration of docetaxel encapsulated in nanoparticles was higher than conventional docetaxel at early timepoints and throughout the 24 hour period in the spleen, the nanoparticles doped with docetaxel were well tolerated at approximately 10 mg/kg docetaxel dose. In addition, body weight changes and clinical observations in the Sprague-Dawley rats indicate that the docetaxel encapsulated in nanoparticles was tolerated as well as conventional docetaxel through a range of acute doses (5-30 mg/kg docetaxel).

were assigned to different treatment groups such that the average tumor volume in each group was 300 mm$^3$. At this time, a single intravenous (IV) dose of 50 mg/kg docetaxel was administered as either docetaxel encapsulated in nanoparticles or conventional docetaxel. The test subjects were sacrificed 2 hour or 12 hour post-dose. The tumors from each group were excised and assayed for docetaxel using liquid chromatography-mass spectrometry (LC-MS).

Figure 6:
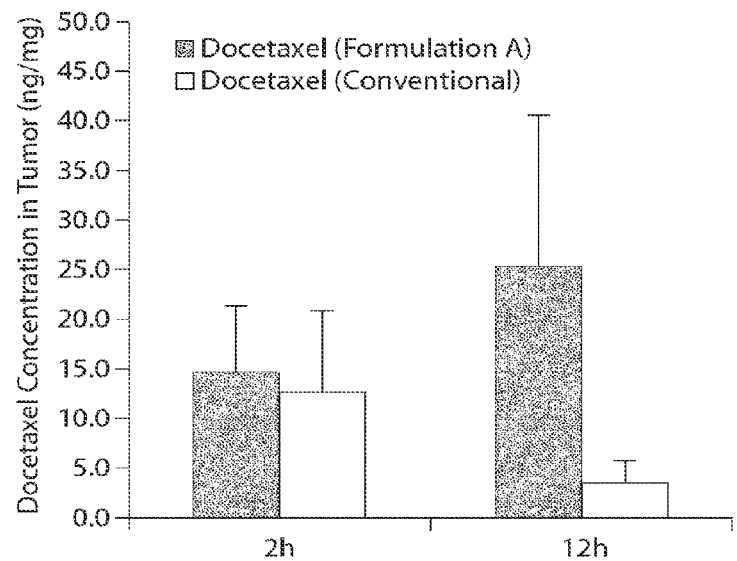
FIG. 6 depicts docetaxel concentration in tumor tissue after administration of docetaxel encapsulated in nanoparticles or conventional docetaxel to LNCaP tumor bearing SCID mice.

The measured docetaxel concentrations in tumors excised from the test subjects dosed with docetaxel encapsulated in nanoparticles or conventional docetaxel are presented in Example Table 4.1 and FIG. 6. At 12 hours post-dose, the tumor docetaxel concentration in test subjects receiving docetaxel encapsulated in nanoparticles was approximately 7

EXAMPLE TABLE 3.1

Tissue Distribution of Radioactivity Determined in Rats after IV Administration of Nanoparticles Containing $^{14}$C-Targeting Polymer.

| Time (h) | Plasma (nCi/mL) | Liver (nCi/g) | Spleen (nCi/g) | Heart (nCi/g) | Lungs (nCi/g) | Bone Marrow (nCi/g) | Small Intestine (nCi/g) | Large Intestine (nCi/g) |
|---|---|---|---|---|---|---|---|---|
| 1  | 2341 ± 168 | 337 ± 14 | 829 ± 26   | 180 ± 23 | 294 ± 78 | 109 ± 25  | 56 ± 2.5 | 36 ± 3.1 |
| 3  | 2023 ± 58  | 334 ± 43 | 1141 ± 75  | 190 ± 62 | 264 ± 38 | 191 ± 122 | 50 ± 5.4 | 33 ± 3.6 |
| 6  | 2001 ± 71  | 364 ± 23 | 1789 ± 173 | 174 ± 25 | 263 ± 40 | 372 ± 8.7 | 48 ± 8.0 | 43 ± 10  |
| 12 | 1445 ± 59  | 375 ± 41 | 2079 ± 205 | 151 ± 21 | 266 ± 24 | 390 ± 58  | 71 ± 3.6 | 40 ± 6.1 |
| 24 | 998 ± 55   | 398 ± 59 | 2808 ± 238 | 119 ± 11 | 218 ± 26 | 594 ± 248 | 88 ± 17  | 38 ± 5.0 |

EXAMPLE TABLE 3.2

Tissue Distribution of Radioactivity Determined in Rats after IV Administration of Nanoparticles Containing $^{14}$C-Docetaxel.

| Time (h) | Plasma (nCi/mL) | Liver (nCi/g) | Spleen (nCi/g) | Heart (nCi/g) | Lungs (nCi/g) | Bone Marrow (nCi/g) | Small Intestine (nCi/g) | Large Intestine (nCi/g) |
|---|---|---|---|---|---|---|---|---|
| 1  | 753 ± 149 | 267 ± 45  | 889 ± 43 | 156 ± 15 | 277 ± 27 | 142 ± 20  | 409 ± 158 | 71 ± 24  |
| 3  | 265 ± 52  | 127 ± 12  | 999 ± 94 | 80 ± 3.6 | 154 ± 9.0 | 127 ± 17 | 219 ± 30  | 151 ± 37 |
| 6  | 140 ± 38  | 88 ± 9.7  | 972 ± 44 | 69 ± 9.8 | 118 ± 23 | 121 ± 5.9 | 119 ± 20  | 133 ± 38 |
| 12 | 24 ± 1.9  | 47 ± 6.3  | 854 ± 56 | 41 ± 2.1 | 58 ± 8.4 | 89 ± 9.3  | 50 ± 2.7  | 98 ± 14  |
| 24 | 5.7 ± 1.0 | 22 ± 3.1  | 634 ± 95 | 23 ± 1.3 | 44 ± 2.5 | 33 ± 8.2  | 43 ± 9.3  | 58 ± 4.9 |

EXAMPLE TABLE 3.3

Tissue Distribution of Radioactivity Determined in Rats after IV Administration of Conventional $^{14}$C-Docetaxel.

| Time (h) | Plasma (nCi/mL) | Liver (nCi/g) | Spleen (nCi/g) | Heart (nCi/g) | Lungs (nCi/g) | Bone Marrow (nCi/g) | Small Intestine (nCi/g) | Large Intestine (nCi/g) |
|---|---|---|---|---|---|---|---|---|
| 1  | 4.9 ± 0.4 | 78 ± 15  | 100 ± 9.4 | 71 ± 2.5 | 82 ± 9.6      | 97 ± 4.2 | 517 ± 99 | 54 ± 3.6 |
| 3  | 1.9 ± 0.2 | 49 ± 7.3 | 81 ± 7.5  | 39 ± 1.5 | 66 ± 0.7      | 83 ± 1.0 | 122 ± 43 | 166 ± 37 |
| 6  | 1.6 ± 0.5 | 49 ± 11  | 82 ± 4.6  | 33 ± 1.3 | 993 ± 1605*   | 78 ± 1.9 | 62 ± 5.2 | 185 ± 82 |
| 12 | 0.8 ± 0.2 | 55 ± 7.4 | 77 ± 11   | 28 ± 1.7 | 1438 ± 1218*  | 62 ± 9.4 | 41 ± 4.9 | 83 ± 18  |
| 24 | 0.6 ± 0.1 | 43 ± 4.0 | 85 ± 8.6  | 24 ± 2.6 | 962 ± 99*     | 41 ± 6.8 | 47 ± 19  | 48 ± 34  |

*Samples likely contaminated during collection/analysis

Example 4

Tumor Targeting of Docetaxel Encapsulated in Nanoparticles and Conventional Docetaxel after a Single Dose in a Human Tumor Xenograft Model (LNCaP)

Male severe combined immunodeficiency (SCID) mice were subcutaneously inoculated with human LNCaP prostate cancer cells. Three to four weeks after inoculation, the mice times higher than in the test subjects receiving conventional docetaxel. These results are consistent with the pharmacokinetic and tissue distribution data as well as the proposed mechanism of action wherein the nanoparticles doped with docetaxel are designed to provide extended particle circulation times and controlled release of docetaxel from the nanoparticles so that particles can be targeted to and bind with a marker or target to increase the amount of docetaxel delivered to the tumor.

EXAMPLE TABLE 4.1

Measured Docetaxel Concentration in Tumors Treated with Docetaxel Encapsulated in Nanoparticles and Conventional Docetaxel

| | Docetaxel Concentration in the Tumor (ng/mg) | |
| --- | --- | --- |
| Time (h) | Conventional Docetaxel | Docetaxel Encapsulated in Nanoparticles |
| 2 | 12.9 ± 7.9 | 14.8 ± 6.5 |
| 12 | 3.6 ± 2.1 | 25.4 ± 15.1 |

Example 5

Anti-tumor Activity of Docetaxel Encapsulated in Nanoparticles and Conventional Docetaxel after Repeated Doses in a Human Tumor Xenograft Model (LNCaP)

Male severe combined immunodeficiency (SCID) mice were subcutaneously inoculated with human LNCaP prostate cancer cells. Three to four weeks after inoculation, the mice were assigned to different treatment groups such that the average tumor volume in each group was 250 mm³. Subsequently, the mice were treated every other day (Q2D) for four doses, with an eight day holiday, followed by another four doses at the Q2D schedule.

Figure 7:
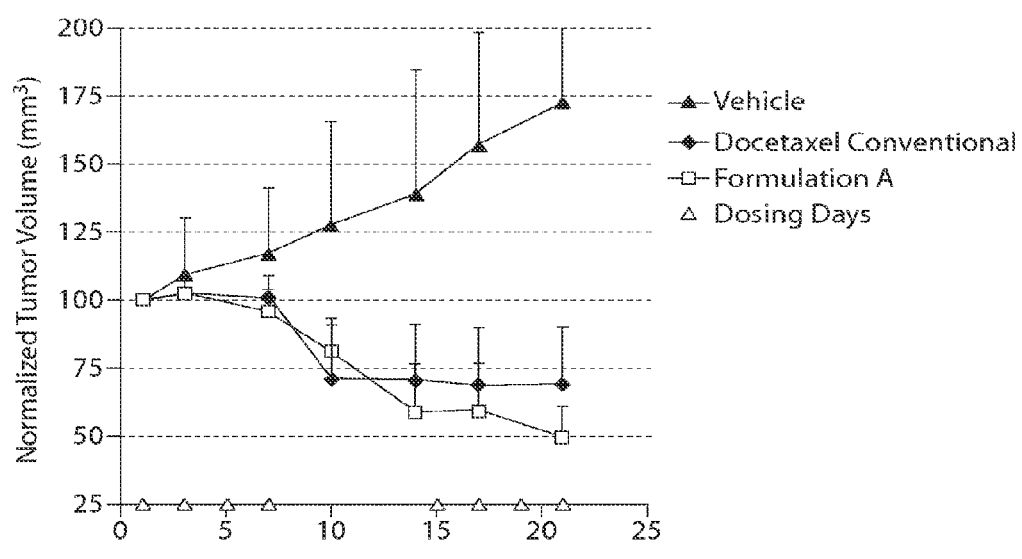
FIG. 7 depicts the reduction in tumor volume in mice with PSMA-expressing LNCaP xenografts when treated with docetaxel encapsulated in nanoparticles or conventional docetaxel.

Average tumor volumes for each treatment group are shown in Example FIG. 7. Treatment with either conventional docetaxel or docetaxel encapsulated in nanoparticles resulted in appreciable reduction in tumor volume. Tumor volume reduction was greater in test subjects receiving docetaxel encapsulated in nanoparticles compared to conventional docetaxel. These results suggest that the increase in tumor docetaxel concentration in test subjects receiving nanoparticles doped with docetaxel, compared to conventional docetaxel, may result in a more pronounced cytotoxic effect.

Example 6

Acute Dose Range Finding Study of Docetaxel Encapsulated in Nanoparticles in Sprague-Dawley Rats Sixty Sprague-Dawley rats (30/sex) were assigned to 10 dose groups (3 rats/sex/group) and were administered a single dose of either docetaxel encapsulated in nanoparticles (5.7, 7.5, 10, 15 or 30 mg/kg body weight) or conventional docetaxel (5.7, 7.5, 10, or 30 mg/kg body weight). The therapeutic compositions were administered by intravenous (IV) infusion over a 30-minute period on Day 1, after which the test subjects were observed for 7 days prior to undergoing a gross necropsy.

All test subjects survived to their scheduled necropsy. Clinical observations considered to be potentially related to administration included piloerection, which appeared near the end of the 7 day observation period, and discharges from the nose and eyes. Piloerection was observed for one male rat dosed with 15 mg/kg of docetaxel encapsulated in nanoparticles, and for 5/9 male rats and 1/9 female rats dosed with 10 mg/kg of conventional docetaxel or higher. The nature and time of appearance of this clinical sign were consistent with toxicity that would be expected from cytotoxic drugs like docetaxel. Nasal and eye discharges appeared with a pattern that was unrelated to dose level, test article, sex of the animals, or time after dosing, and this clinical sign was considered to be possibly related to docetaxel and/or to stress from the dosing procedure. As shown in Example Table 6.1, male and female rats dosed with either conventional docetaxel or docetaxel encapsulated in nanoparticles showed generally minor deficits in body weight gain or actual body weight losses that were considered to be due to docetaxel toxicity. The no-adverse effect level (NOAEL) of nanoparticles doped with docetaxel in this study was considered to be 7.5 mg/kg.

EXAMPLE TABLE 6.1

Comparison of Body Weight Changes in Males and Females

| Sex | Dose (mg/kg) | Docetaxel Encapsulated in Nanoparticles Body Weight Change (%) | Conventional Docetaxel Body Weight Change (%) |
| --- | --- | --- | --- |
| M | 5.7 | 4.60 | 8.60 |
| M | 7.5 | 1.67 | 1.21 |
| M | 10 | −3.15 | −11.55 |
| M | 15 | −6.23 | −9.48 |
| M | 30 | −7.16 | −8.66 |
| F | 5.7 | 3.63 | 0.34 |
| F | 7.5 | 3.25 | −0.11 |
| F | 10 | −2.49 | −0.17 |
| F | 15 | −2.50 | −6.86 |
| F | 30 | −5.66 | −5.89 |

Example 7

Pharmacokinetics of Vincristine Passively Targeted Nanoparticles in Rats

Figure 8:
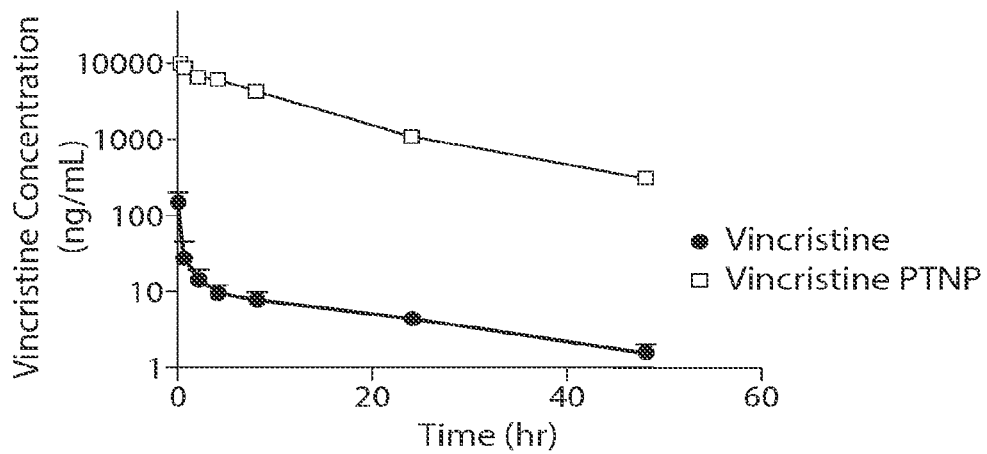
FIG. 8 depicts pharmacokinetics of vincristine encapsulated in disclosed nanoparticles and conventional vincristine in rats.

Similar to the procedure in Example 2, rats were intravenously dosed with 0.5 mg/kg with either nanoparticles prepared as in FIG. 2 and Example 14 having vincristine and PLA-PEG, and no specific targeting moiety (passively targeted nanoparticles (PTNP); or vincristine alone. The release profiles are shown in FIG. 8.

Plasma samples were analyzed using LC/MS and the PK analysis was performed using WinNonlin software. A comparison of the pharmacokinetics of the nanoparticles with vincristine alone is as follows:

| | Comparison with vincristine alone |
| --- | --- |
| $C_{max}$ (ng/mL) | 69-fold ↑ |
| $t_{1/2}$ (hr) | 1.8-fold ↓ |
| $AUC_{inf}$ (hr*ng/mL) | 312-fold ↑ |
| $V_z$ (mL/kg) | 592-fold ↓ |
| Cl (mL/hr/kg) | 322-fold ↓ |

Example 8

Pharmacokinetics of Methotrexate Passively Targeted Nanoparticles in Rats

Figure 9:
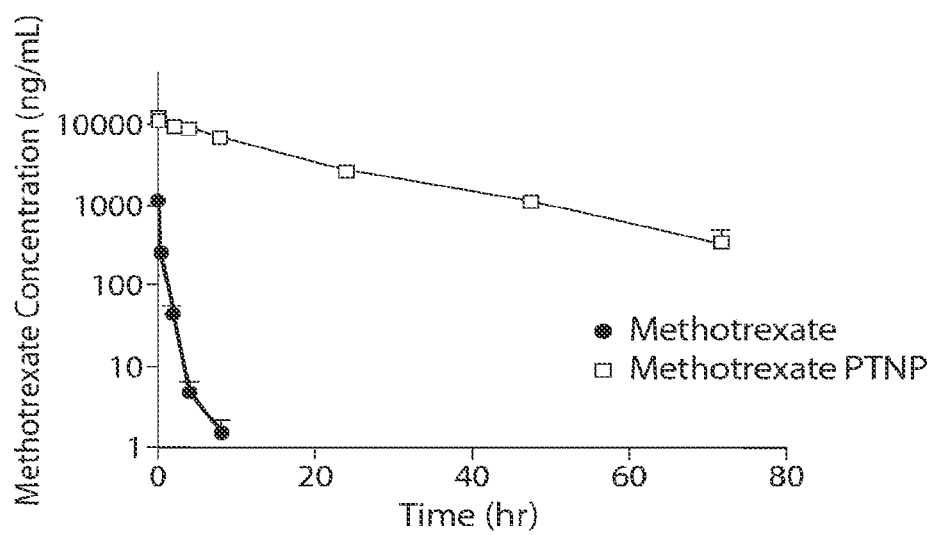
FIG. 9 depicts pharmacokinetics of methotrexate encapsulated in disclosed nanoparticles and conventional methotrexate in rats.

Similar to the procedure in Example 2, rats were intravenously dosed with 0.5 mg/kg with either nanoparticles prepared as in FIG. 2 and Example 15 having methotrexate and PLA-PEG, and no specific targeting moiety (passively targeted nanoparticles (PTNP); or methotrexate alone. The release profiles are shown in FIG. 9.

Plasma samples were analyzed using LC/MS and the PK analysis was performed using WinNonlin software. A comparison of the pharmacokinetics of the nanoparticles with methotrexate alone is as follows:

| | Comparison with methotrexate alone |
|---|---|
| $C_{max}$ (ng/mL) | 10-fold ↑ |
| $t_{1/2}$ (hr) | 16-fold ↓ |
| $AUC_{inf}$ (hr*ng/mL) | 296-fold ↑ |
| $V_z$ (mL/kg) | 19-fold ↓ |
| Cl (mL/hr/kg) | 302-fold ↓ |

Example 9

Pharmacokinetics of Paclitaxel Passively Targeted Nanoparticles in Rats

Figure 10:
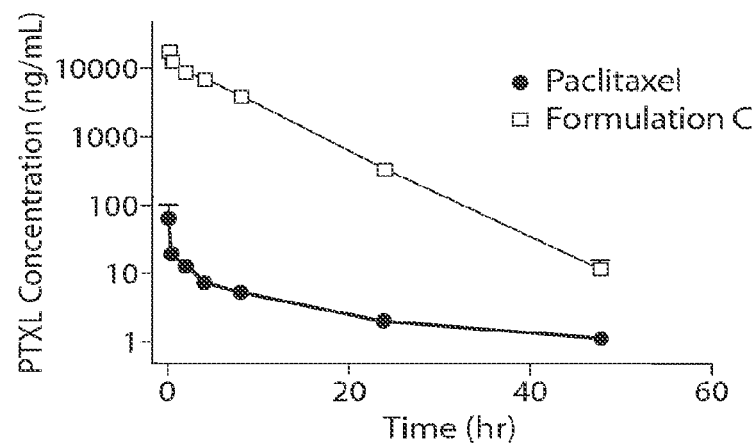
FIG. 10 depicts pharmacokinetics of paclitaxel encapsulated in disclosed nanoparticles and conventional paclitaxel in rats.

Similar to the procedure in Example 2, rats were intravenously dosed with 1.0 mg/kg with either nanoparticles prepared as in FIG. 2 having paclitaxel and PLA-PEG (formulation C) and no specific targeting moiety (passively targeted nanoparticles (PTNP); or paclitaxel alone. The release profiles are shown in FIG. 10.

Plasma samples were analyzed using LC/MS and the PK analysis was performed using WinNonlin software. A comparison of the pharmacokinetics of the nanoparticles with paclitaxel alone is as follows:

| | Comparison with paclitaxel alone |
|---|---|
| $C_{max}$ (ng/mL) | 297-fold ↑ |
| $t_{1/2}$ (hr) | 3-fold ↓ |
| $AUC_{inf}$ (hr*ng/mL) | 600-fold ↑ |
| $V_z$ (mL/kg) | 1512-fold ↓ |
| Cl (mL/hr/kg) | 516-fold ↓ |

Example 10

Figure 11:
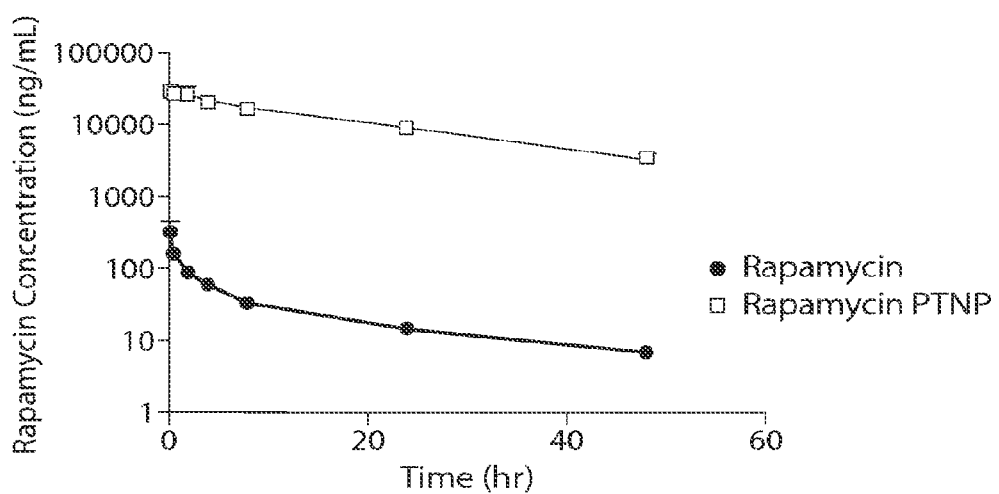
FIG. 11 depicts pharmacokinetics of rapamycin (sirolimus) encapsulated in disclosed nanoparticles and conventional rapamycin in rats.

Pharmacokinetics of Rapamycin (Sirolimus) Passively Targeted Nanoparticles in Rats Similar to the procedure in Example 2, rats were intravenously dosed with 2.0 mg/kg with either nanoparticles prepared as in FIG. 2 and Example 16, having rapamycin and PLA-PEG and no specific targeting moiety (passively targeted nanoparticles (PTNP); or rapamycin alone. The release profiles are shown in FIG. 11.

Plasma samples were analyzed using LC/MS and the PK analysis was performed using WinNonlin software. A comparison of the pharmacokinetics of the nanoparticles with rapamcyin alone is as follows:

| | Comparison with rapamcyin alone |
|---|---|
| $C_{max}$ (ng/mL) | 297-fold ↑ |
| $t_{1/2}$ (hr) | 3-fold ↓ |
| $AUC_{inf}$ (hr*ng/mL) | 600-fold ↑ |
| $V_z$ (mL/kg) | 1512-fold ↓ |
| Cl (mL/hr/kg) | 516-fold ↓ |

Example 11

Tumor Accumulation of Docetaxel Nanoparticles in MX-1 Breast Tumors in Mice

Figure 12:
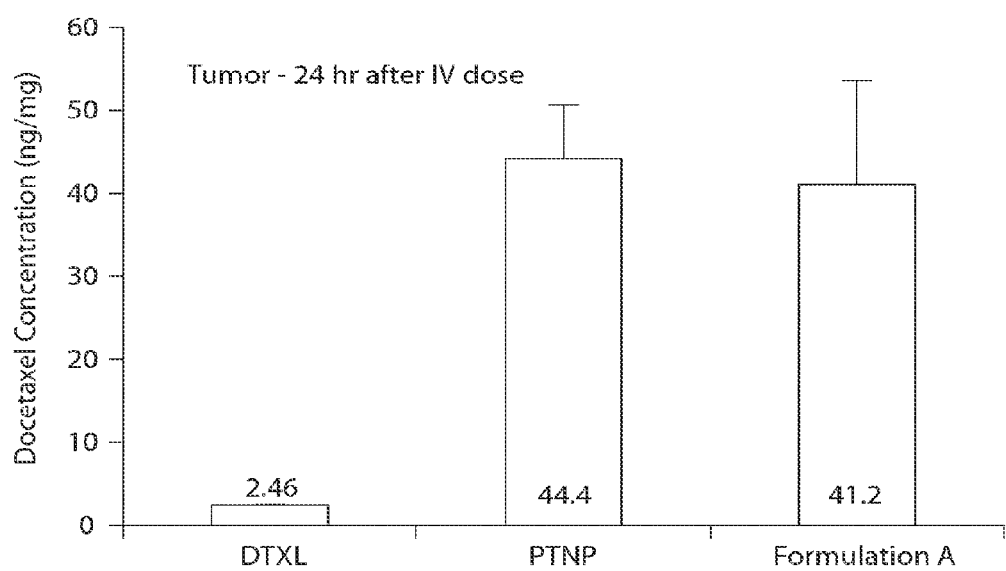
FIG. 12 depicts the tumor accumulation of docetaxel in disclosed nanoparticles in a MX-1 mouse breast tumor model.
Figure 13:
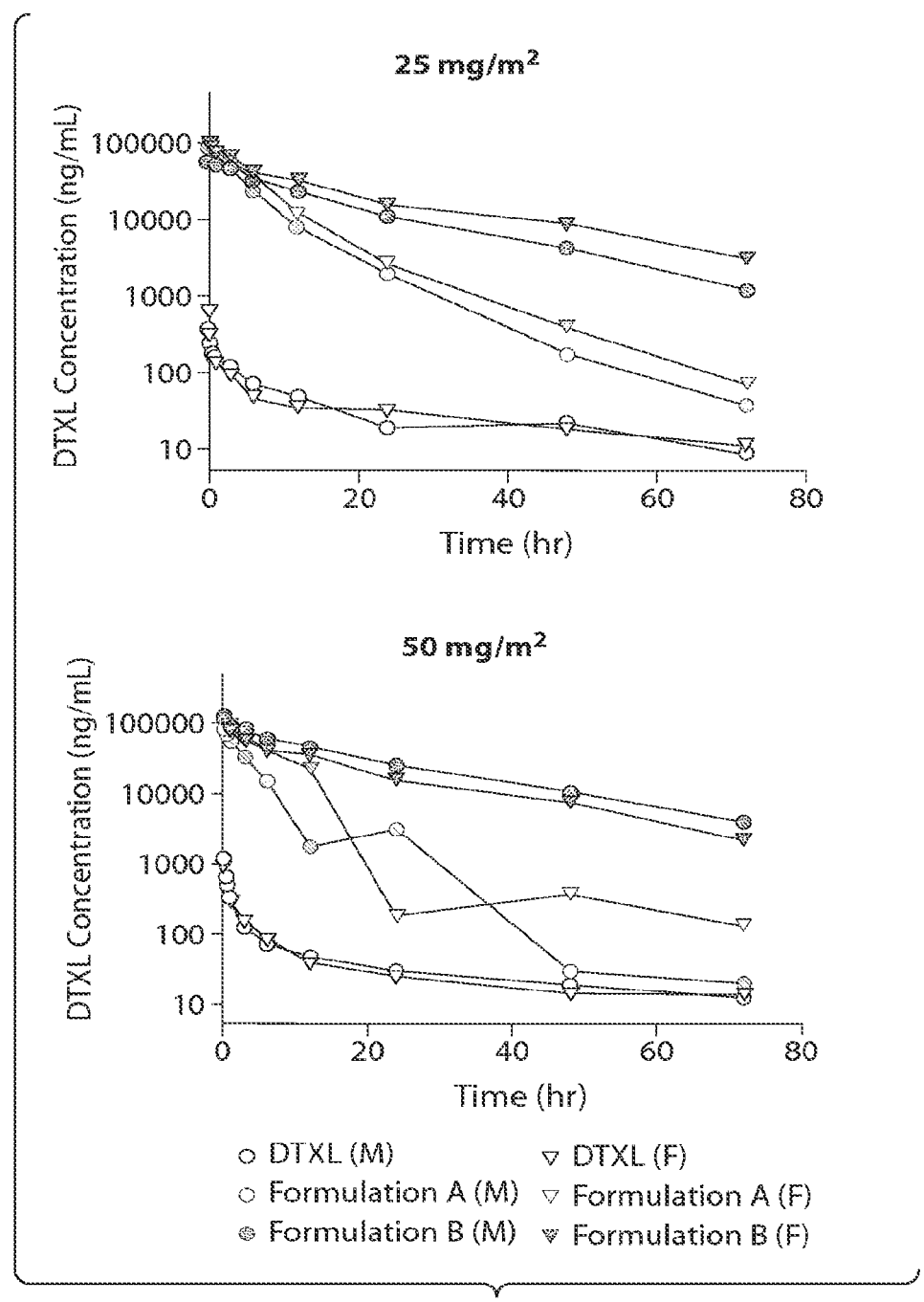
FIG. 13 depicts pharmacokinetics of docetaxel in a NHP model using various disclosed nanoparticles.

Mice with MX-1 breast tumors were randomized into three groups, receiving docetaxel (3 mice), passively targeted nanoparticles (Formulation A, without a targeting moiety, PTNP), or Formulation A. The average tumor mass was 1.7 g (RSD 34%). Mice were then injected with 10 mg/kg of the test article, then euthanized 24 hours later and the tumors were removed and analyzed for docetaxel content using LC/MS/MS. Results are depicted in FIG. 12. The percent of injected dose in the tumor was 3% (for docetaxel alone), 30% for PTNP, and 30% Formulation A.

Example 12

Pharmacokinetics of Docetaxel Nanoparticles in Primates

Naïve non human primates (3 male and 3 female) were administered docetaxel, docetaxel nanoparticles (Formulation A) or docetaxel nanoparticles (Formulation B: 43.25% PLA-PEG (16/5), 43.25% PLA (75 kDa), 10% docetaxel, 2.5% PLA-PEG-lys(urea)glu, prepared as in Example 14), using and following appropriate ethical guidelines at all times. 1 male and 1 female were used per dose group. The dosing day was 1 day and the formulations were administered by 30 minute IV infusion at 25 mg/m² docetaxel or 50 mg/m² docetaxel (animals were randomized and then dosed with 50 mg/m2 on day 29 and PK, hematology and clinical chemistry were measured for 21 days). At the end of the study, PK, hematology and clinical chemistry collected over a 21 day period were assessed. FIG. 12 depicts the results of male (M) and female (F) PNP. A comparison of the pharmacokinetics of the nanoparticles of Formulation A (25 mg/m² dose) with docetaxel alone is as follows:

| | Comparison with docetaxel alone |
|---|---|
| $C_{max}$ (ng/mL) | 180-fold ↑ |
| $t_{1/2}$ (hr) | 3-fold ↓ |
| $AUC_{inf}$ (hr*ng/mL) | 213-fold ↑ |
| $V_z$ (mL/kg) | 617-fold ↓ |
| Cl (mL/hr/kg) | 212-fold ↓ |

The pharmacokinetics were as follows for each NHP group:

| | A. Docetaxel alone | | | |
|---|---|---|---|---|
| | 25 mg/m2 | | 50 mg/m2 | |
| | M | F | M | F |
| $C_{max}$ (ng/mL) | 364 | 596 | 1210 | 835 |
| $C_{max}$/D | 14.6 | 23.8 | 24.2 | 16.7 |
| AUC (hr*ng/mL) | 2553 | 2714 | 3285 | 3599 |
| AUC/D | 102 | 109 | 76.5 | 72 |
| $t_{1/2}$ (hr) | 18 | 31 | 39 | 39 |
| $V_z$ (mL/m2) | 253783 | 412186 | 743682 | 788340 |
| Cl (mL/hr/m2) | 9794 | 9213 | 13073 | 13893 |

| | B. Formulation A | | | |
|---|---|---|---|---|
| | 25 mg/m2 | | 50 mg/m2 | |
| | M | F | M | F |
| $C_{max}$ (ng/mL) | 89500 | 85500 | 95700 | 117000 |
| $C_{max}$/D | 3580 | 3420 | 1914 | 2340 |
| AUC (hr*ng/mL) | 495408 | 627216 | 352778 | 748073 |
| AUC/D | 19816 | 25089 | 7056 | 14961 |
| $t_{1/2}$ (hr) | 7.6 | 9.1 | 5.6 | 6.8 |
| $V_z$ (mL/m2) | 554 | 526 | 1140 | 654 |
| Cl (mL/hr/m2) | 50 | 40 | 142 | 67 |

C. Formulation B

|  | 25 mg/m2 | | 50 mg/m2 | |
| --- | --- | --- | --- | --- |
|  | M | F | M | F |
| $C_{max}$ (ng/mL) | 64500 | 101500 | 128000 | 116000 |
| $C_{max}/D$ | 2580 | 4060 | 2560 | 2320 |
| AUC (hr*ng/mL) | 956312 | 1442885 | 1960145 | 1395580 |
| AUC/D | 38252 | 57715 | 39203 | 27912 |
| $t_{1/2}$ (hr) | 13.9 | 17.8 | 17.8 | 15.5 |
| $V_z$ (mL/m2) | 525 | 445 | 657 | 803 |
| Cl (mL/hr/m2) | 26.1 | 17.3 | 25.5 | 35.8 |

Example 13

Preparation of Docetaxel Nanoparticles

An organic phase is formed composed of a mixture of docetaxel (DTXL) and polymer (homopolymer, co-polymer, and co-polymer with ligand). The organic phase is mixed with an aqueous phase at approximately a 1:5 ratio (oil phase: aqueous phase) where the aqueous phase is composed of a surfactant and some dissolved solvent. In order to achieve high drug loading, about 30% solids in the organic phase is used.

The primary, coarse emulsion is formed by the combination of the two phases under simple mixing or through the use of a rotor stator homogenizer. The rotor/stator yielded a homogeneous milky solution, while the stir bar produced a visibly larger coarse emulsion. It was observed that the stir bar method resulted in significant oil phase droplets adhering to the side of the feed vessel, suggesting that while the coarse emulsion size is not a process parameter critical to quality, it should be made suitably fine in order to prevent yield loss or phase separation. Therefore the rotor stator is used as the standard method of coarse emulsion formation, although a high speed mixer may be suitable at a larger scale.

The primary emulsion is then formed into a fine emulsion through the use of a high pressure homogenizer.

After 2-3 passes the particle size was not significantly reduced, and successive passes can even cause a particle size increase. Organic phase was emulsified 5:1 O:W with standard aqueous phase, and multiple discreet passes were performed, quenching a small portion of emulsion after each pass. The indicated scale represents the total solids of the formulation.

The effect of scale on particle size showed surprising scale dependence. The trend shows that in the 2-10 g batch size range, larger batches produce smaller particles. It has been demonstrated that this scale dependence is eliminated when considering greater than 10 g scale batches. The amount of solids used in the oil phase was about 30%. FIGS. 8 and 9 depicts the effect of solids concentration on particle size and drug loading; with the exception of the 15-175 series, all batches are placebo. For placebo batches the value for % solids represents the % solids were drug present at the standard 20% w/w.

Table A summarizes the emulsification process parameters.

TABLE A

| Parameter | Value |
| --- | --- |
| Coarse emulsion formation | Rotor stator homogenizer |
| Homogenizer feed pressure | 4000-5000 psi per chamber |

TABLE A-continued

| Parameter | Value |
| --- | --- |
| Interaction chamber(s) | 2 × 200 µm Z-chamber |
| Number of homogenizer passes | 2-3 passes |
| Water phase [sodium cholate] | 0.1% |
| W:O ratio | 5:1 |
| [Solids] in oil phase | 30% |

The fine emulsion is then quenched by addition to deionized water at a given temperature under mixing. In the quench unit operation, the emulsion is added to a cold aqueous quench under agitation. This serves to extract a significant portion of the oil phase solvents, effectively hardening the nanoparticles for downstream filtration. Chilling the quench significantly improved drug encapsulation. The quench: emulsion ratio is approximately 5:1.

A solution of 35% (wt %) of Tween 80 is added to the quench to achieve approximately 2% Tween 80 overall After the emulsion is quenched a solution of Tween-80 is added which acts as a drug solubilizer, allowing for effective removal of unencapsulated drug during filtration. Table B indicates each of the quench process parameters.

TABLE B

Summary quench process parameters.

| Parameter | Value |
| --- | --- |
| Initial quench temperature | <5° C. |
| [Tween-80] solution | 35% |
| Tween-80:drug ratio | 25:1 |
| Q:E ratio | 5:1 |
| Quench hold/processing temp | ≤5° C. (with current 5:1 Q:E ratio, 25:1 Tween-80:drug ratio) |

The temperature must remain cold enough with a dilute enough suspension (low enough concentration of solvents) to remain below the $T_g$ of the particles. If the Q:E ratio is not high enough, then the higher concentration of solvent plasticizes the particles and allows for drug leakage. Conversely, colder temperatures allow for high drug encapsulation at low Q:E ratios (to ~3:1), making it possible to run the process more efficiently.

The nanoparticles are then isolated through a tangential flow filtration process to concentrate the nanoparticle suspension and buffer exchange the solvents, free drug, and drug solubilizer from the quench solution into water. A regenerated cellulose membrane is used with a molecular weight cutoffs (MWCO) of 300.

A constant volume diafiltration (DF) is performed to remove the quench solvents, free drug and Tween-80. To perform a constant-volume DF, buffer is added to the retentate vessel at the same rate the filtrate is removed. The process parameters for the TFF operations are summarized in Table C. Crossflow rate refers to the rate of the solution flow through the feed channels and across the membrane. This flow provides the force to sweep away molecules that can foul the membrane and restrict filtrate flow. The transmembrane pressure is the force that drives the permeable molecules through the membrane.

TABLE C

TFF Parameters

| Parameter | Value |
| --- | --- |
| Membrane Material | Regenerated cellulose - Coarse Screen Membrane |
| Molecular Weight Cut off | 300 kDa |
| Crossflow Rate | 11 L/min/m$^2$ |
| Transmembrane Pressure | 20 psid |
| Concentration of Nanoparticle Suspension for Diafiltration | 30 mg/ml |
| Number of Diavolumes | ≥15 (based on flux increase) |
| Membrane Area | ~1 m$^2$/kg |

The filtered nanoparticle slurry is then thermal cycled to an elevated temperature during workup. A small portion (typically 5-10%) of the encapsulated drug is released from the nanoparticles very quickly after its first exposure to 25° C. By exposing the nanoparticle slurry to elevated temperature during workup, 'loosely encapsulated' drug can be removed and improve the product stability at the expense of a small drop in drug loading.

After the filtration process the nanoparticle suspension (concentration 50 mg/ml), is passed through a sterilizing grade filter (0.2 μm absolute). Pre-filters are used to protect the sterilizing grade filter in order to use a reasonable filtration area/time for the process. Filtration flow rate is ~1.3 L/min/m$^2$.

The filtration train is Ertel Alsop Micromedia XL depth filter M953P membrane (0.2 μm Nominal); Pall SUPRAcap with Seitz EKSP depth filter media (0.1-0.3 μm Nominal); Pall Life Sciences Supor EKV 0.65/0.2 micron sterilizing grade PES filter. 0.2 m$^2$ of filtration surface area per kg of nanoparticles for depth filters and 1.3 m$^2$ of filtration surface area per kg of nanoparticles for the sterilizing grade filters can be used.

Example 14

Preparation of Nanoparticles with Long Release Properties

The nanoparticle preparation protocol described in Example 12 was modified to produce slow release nanoparticles.

A batch of nanoparticles was produced that incorporated a 50:50 ratio of 100 DL 7E PLA (see Table 1) with the 16/5 PLA-PEG copolymer. The addition of high molecular weight PLA is thought to decrease drug diffusion by increasing crystallinity, raising the glass transition temperature, or reducing drug solubility in the polymer.

TABLE 1

High Molecular Weight PLA Tested

| PLA | Manufacturer | Molecular Weight (Mn) | Molecular Weight (Mw) |
| --- | --- | --- | --- |
| 100 DL 7E | Lakeshore Polymer | 80 kDa | 124 kDa |

The addition of high molecular weight PLA resulted in larger particle size when all other formulation variables were kept constant. In order to obtain slow release nanoparticles with comparable sizes as nanoparticles prepared without the high molecular weight PLA, the concentration of solids in the oil phase was reduced and the concentration of sodium cholate in the water phase was increased. Table 2 illustrates the slow release nanoparticle formulation.

TABLE 2

Slow Release Formulation Summary

| Polymers Used | % Solids in Oil Phase | % Sodium Cholate in Water Phase | % Drug Load | Particle Size (nm) |
| --- | --- | --- | --- | --- |
| 50% BI 16/5 PLA-PEG 50% Lakeshore 100 DL 7E PLA | 20% | 2.0% | 11.7% | 139.8 |

Example 14

Nanoparticles with Vincristine

Nanoparticle batches were prepared using the general procedure of Example 12, with 80% (w/w) Polymer-PEG or Polymer-PEG with homopolymer PLA at 40% (w/w) each, with a batch of % total solids of 5%, 15% and 30%. Solvents used were: 21% benzyl alcohol and 79% ethyl acetate (w/w). For each 2 gram batch size, 400 mg of drug was used and 1.6 g of 16-5 Polymer-PEG or 0.8 g of 16-5 Polymer-PEG+0.8 g of 10 kDa PLA (homopolymer) was used. The diblock polymer 16-5 PLA-PEG or PLGA-PEG (50:50 L:G) was used, and if used, the homopolymer: PLA with a Mn=6.5 kDa, Mw=10 kDa, and Mw/Mn=1.55.

The organic phase (drug and polymer) is prepared in 2 g batches: To 20 mL scintillation vial add drug and polymer(s). The mass of solvents needed at % solids concentration is: 5% solids: 7.98 g benzyl alcohol+30.02 g ethyl acetate; 30% solids: 0.98 g benzyl alcohol+3.69 g ethyl acetate An aqueous solution is prepared with 0.5% sodium cholate, 2% benzyl alcohol, and 4% ethyl acetate in water. Add to the bottle 7.5 g sodium cholate, 1402.5 g of DI water, 30 g of benzyl alcohol and 60 g of ethyl acetate, and mix on stir plate until dissolved.

For the formation of emulsion, a ratio of aqueous phase to oil phase is 5:1. The organic phase is poured into the aqueous solution and homogenized using IKA for 10 seconds at room temperature to form course emulsion. The solution is fed through the homogenizer (110S) at 9 Kpsi (45 psi on gauge) for 2 discreet passes to form nanoemulsion.

The emulsion is poured into quench (D.I. water) at <5° C. while stirring on stir plate. Ratio of quench to emulsion is 8:1.35% (w/w) Tween 80 is added in water to quench at ratio of 25:1 Tween 80 to drug. The nanoparticles are concentrated through TFF and the quench is concentrated on TFF with 500 kDa Pall cassette (2 membrane) to ~100 mL. Diafiltering is used using ~20 diavolumes (2 liters) of cold DI water, and the volume is brought down to minimal volume then collect final slurry, ~100 mL. The solids concentration of unfiltered final slurry is determined by the using tared 20 mL scintillation vial and adding 4 mL final slurry and dry under vacuum on lyo/oven and the weight of nanoparticles in the 4 mL of slurry dried down is determined. Concentrated sucrose (0.666 g/g) is added to final slurry sample to attain 10% sucrose.

Solids concentration of 0.45 um filtered final slurry was determined by filtering about 5 mL of final slurry sample before addition of sucrose through 0.45 μm syringe filter; to tared 20 mL scintillation vial add 4 mL of filtered sample and dry under vacuum on lyo/oven.

The remaining sample of unfiltered final slurry was frozen with sucrose.

Vincristine Formulations

| Components | Composition by Wt.(%) |
|---|---|
| mPEG(5k)-lPLA(16K)/Vincristine | 96/4 |
| mPEG(5k)-lPLA(16K)/Vincristine | 95/5 |
| mPEG(5k)-lPLA(16K)/Vincristine | 96/4 |
| mPEG(5k)-lPLA(16K)/lPLA(16K)/Vincristine | 46/46/8 |
| mPEG(5k)-lPLA(16K)/lPLA(16K)/Vincristine | 47/47/6 |

Analytical Characterization of Vincristine Formulations:

| Size (nm) | Drug Load (%) | Encapsulation Efficiency (%) |
|---|---|---|
| 103 | 4.4 | 21.8 |
| 110 | 4.6 | 22.8 |
| 115 | 4.2 | 20.8 |
| 146 | 8.3 | 41.6 |
| 98 | 6.0 | 30.0 |

Example 15

Nanoparticles with Methotrexate

Drug was dissolved in the inner aqueous phase consisting of water with 1-arginine or NaOH used for solubilizing the drug. The polymer (16-5 PLA-PEG) was dissolved in the oil phase organic solvent system, such as dichloromethane (DCM) at 20% solid concentration. The outer aqueous phase consisted mainly of water with 1% sodium cholate (SC) as surfactant, unless noted otherwise. The w/o emulsion was prepared by adding the inner aqueous phase into the oil phase under rotor stator homogenization or sonication (using Branson Digital Sonifier) at a w/o ratio of 1:10. The coarse w/o/w emulsion was also prepared by adding the w/o emulsion into an outer aqueous phase under either rotor stator homogenization or sonication at o/w ratio of 1:10. The fine w/o/w emulsion was then prepared by processing the coarse emulsion through a Microfluidics high pressure homogenizer (M110S pneumatic) at 45000 psi with a 100 µm Z-interaction chamber. The fine emulsion was then quenched into cold DI water at 10:1 quench:emulsion ratio. These w/o, o/w and emulsion: quench ratios were maintained at 1:10 for all w/o/w experiments, unless noted otherwise. Polysorbate 80 (Tween 80) was then added as a process solubilizer to solubilize the unencapsulated drug. No drug precipitation was observed at a drug:Tween 80 ratio of 1:200. The batch was then processed with ultrafiltration followed by diafiltration to remove solvents, unencapsulated drug and solubilizer. The particle size measurements were performed by Brookhaven DLS and/or Horiba laser diffraction. To determine drug load, slurry samples were analyzed by HPLC and solid concentration analysis. The slurry retains were then diluted with sucrose to 10% before freezing. All ratios listed are on a w/w basis, unless specified otherwise.

Using 16/5 PLA-PEG dissolved in ethyl acetate afforded particles between 77-85 nm in size at ≤6% solid concentration in an outer aqueous phase consisting of 1% SC in DI water. Emulsions were formed under sonication at 30% amplitude. Gel formation occurred in the initial w/o emulsion with ≥6% solid concentration. The inner aqueous phase MTX concentration was increased to 225 mg/ml using 1-arginine. The batch was made with 20% solids in the oil phase, consisting of 28/5 PLGA-PEG dissolved in DCM. Here, both the inner w/o and outer w/o/w emulsions were formed by rotor stator homogenization followed by 2 passes at 45 k psi using a high pressure homogenizer. The nanoparticle suspension was quenched in cold DI water followed by ultrafiltration/diafiltration work-up. HPLC and PSD analysis was used to determine that the drug load stayed at 0.38% for 131 nm particles.

Three different batches can be prepared according to the general procedure with the following modifications; Inner aqueous phase MTX concentration was 225 mg/ml in 0.66N NaOH solution, i.e., a 1-arginine:MTX molar ratio of 1.45:1; Span 80/Tween 80 surfactant mix (HLB=6.2) was used as the oil phase surfactant; Batch 55-101C: 16/5 PLA-PEG was used instead of 28/5 PLGA-PEG. The emulsion process for all three batches remained similar. The highest drug load was obtained for the 16/5 PLA-PEG batch at 2.23% while the drug load was 0.2% and 0.04% for other batches.

Example 16

Preparation of Sirolimus Nanoparticles

An organic phase is formed composed of a mixture of sirolimus and polymer (homopolymer, co-polymer, and co-polymer with ligand). The organic phase is mixed with an aqueous phase at approximately a 1:5 ratio (oil phase:aqueous phase) where the aqueous phase is composed of a surfactant and some dissolved solvent. In order to achieve high drug loading, about 30% solids in the organic phase is used. The primary, coarse emulsion is formed by the combination of the two phases under simple mixing or through the use of a rotor stator homogenizer.

The primary emulsion is then formed into a fine emulsion through the use of a high pressure homogenizer. The process is continued as in Example 12.

Representative Rapamycin (Sirolimus) Formulations:

| Name | Polymer | Size (nm) | Drug Loading |
|---|---|---|---|
| 5% Solid | 16/5 PLA/PEG | 123.1 | 3.61% |
| | 16/5 PLA/PEG + PLA | 119.7 | 4.49% |
| 15% Solid | 16/5 PLA/PEG | 82.1 | 4.40% |
| | 16/5 PLA/PEG + PLA | 120.6 | 11.51% |
| 23% Solid | 16/5 PLA/PEG | 88.1 | 7.40% |
| | 16/5 PLA/PEG + PLA | 118.3 | 7.8% |
| 30% Solid | 16/5 PLA/PEG | 88.5 | 10.26% |
| | 16/5 PLA/PEG + PLA | 118.3 | 10.18% |

Although the invention has been described in considerable detail with reference to certain preferred aspects thereof, other versions are possible. Therefore the spirit and scope of the appended claims should not be limited to the description and the preferred versions contained within this specification.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A sterile, biocompatible, injectable nanoparticle composition comprising a plurality of long circulating nanoparticles having a diameter of about 70 to about 130 nm, each of the plurality of the long circulating nanoparticles comprising:
   about 70 to about 90 weight percent poly(lactic)acid-co-poly(ethylene)glycol, wherein the weight ratio of poly(lactic)acid to poly(ethylene)glycol is about 15 kDa/2 kDa to about 20 kDa/10 kDa, and
   a therapeutic agent encapsulated in the nanoparticles.

2. The sterile, biocompatible, injectable nanoparticle composition of claim 1, wherein each of the plurality of nanoparticles comprise about 5 to about 25 weight percent therapeutic agent.

3. The sterile, biocompatible, injectable nanoparticle composition of claim 1, wherein the weight ratio of poly(lactic) acid to poly(ethylene)glycol in each of the plurality of nanoparticles is about 15 kDa/4 kDa to about 20 kDa/6 kDa.

4. The sterile, biocompatible, injectable nanoparticle composition of claim 1, wherein the weight ratio of poly(lactic) acid to poly(ethylene)glycol in each of the plurality of nanoparticles is about 16 kDa/5 kDa.

5. The sterile, biocompatible, injectable nanoparticle composition of claim 1, wherein the composition is an aqueous solution further comprising a saccharide.

6. The sterile, biocompatible, injectable nanoparticle composition of claim 1, further comprising a surfactant.

7. The sterile, biocompatible, injectable nanoparticle composition of claim 6, wherein the surfactant is polysorbate 80.

8. The sterile, biocompatible, injectable nanoparticle composition of claim 1, wherein therapeutic agent is a chemotherapeutic agent.

9. A sterile, biocompatible, injectable nanoparticle composition comprising a plurality of long circulating nanoparticles, each long circulating nanoparticle comprising:
   about 70 to about 90 weight percent of an $\alpha$-hydroxy polyester-co-polyether comprising a weight ratio of about 16/5 polylactic acid-polyethylene glycol, and docetaxel.

10. A method of treating a solid tumor cancer, comprising administering the nanoparticle composition of claim 1, to a patient in need thereof.

11. The method of claim 10, wherein at least 24 hours after administration, the solid tumor has a concentration of therapeutic agent at least about 20% more than a concentration of therapeutic agent in the tumor after administration of free therapeutic agent.

* * * * *